(12) United States Patent
Nakayama et al.

(10) Patent No.: US 11,259,766 B2
(45) Date of Patent: Mar. 1, 2022

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventors: Hiroki Nakayama, Kanagawa (JP); Tomoki Inoue, Kanagawa (JP); Tomonari Sendai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 141 days.

(21) Appl. No.: 16/855,816

(22) Filed: Apr. 22, 2020

(65) Prior Publication Data
US 2020/0337662 A1      Oct. 29, 2020

(30) Foreign Application Priority Data

Apr. 25, 2019 (JP) .............................. JP2019-083995

(51) Int. Cl.
| | |
|---|---|
| *A61B 6/00* | (2006.01) |
| *A61B 6/02* | (2006.01) |
| *A61B 6/04* | (2006.01) |
| *A61B 6/03* | (2006.01) |

(52) U.S. Cl.
CPC .............. *A61B 6/502* (2013.01); *A61B 6/025* (2013.01); *A61B 6/032* (2013.01); *A61B 6/0414* (2013.01); *A61B 6/4452* (2013.01); *A61B 6/463* (2013.01)

(58) Field of Classification Search
CPC ...... A61B 6/025; A61B 6/0414; A61B 8/5269
See application file for complete search history.

(56) References Cited

U.S. PATENT DOCUMENTS

| | | | |
|---|---|---|---|
| 2011/0216879 A1 | 9/2011 | Jing et al. | |
| 2012/0033868 A1* | 2/2012 | Ren ....................... | A61B 6/5223 382/131 |

FOREIGN PATENT DOCUMENTS

| | | |
|---|---|---|
| JP | 2006-519625 A | 8/2006 |
| JP | 2012-235960 A | 12/2012 |

\* cited by examiner

*Primary Examiner* — Dani Fox
(74) *Attorney, Agent, or Firm* — Studebaker & Brackett PC

(57) ABSTRACT

An image acquisition unit acquires a plurality of projection images corresponding to each of a plurality of radiation source positions which have been generated by directing an imaging apparatus to perform tomosynthesis imaging for an object compressed by a compression plate. An edge image detection unit detects an edge image caused by the edge of the compression plate in the plurality of projection images. A cutout unit cuts out the projection image according to a positional relationship between the edge image and an image of the object to generate a cut-out projection image.

19 Claims, 22 Drawing Sheets

IMAGE PROCESSING APPARATUS, IMAGE PROCESSING METHOD, AND IMAGE PROCESSING PROGRAM

CROSS REFERENCE TO RELATED APPLICATIONS

The present application claims priority under 35 U.S.C. § 119 to Japanese Patent Application No. 2019-083995 filed on Apr. 25, 2019. The above application is hereby expressly incorporated by reference, in its entirety, into the present application.

BACKGROUND

Technical Filed

The present disclosure relates to an image processing apparatus, an image processing method, and an image processing program that perform image processing for a projection image acquired by tomosynthesis imaging.

Related Art

In recent years, image diagnosis using a radiography apparatus (called mammography) for capturing an image of the breast has attracted attention in order to promote early detection of breast cancer. In mammography, imaging is performed in a state in which the breast is placed on an imaging table and is compressed by a compression plate. The breast mainly includes mammary gland tissues and fat tissues and it is important to find lesions, such as tumor mass and calcification, hidden in the mammary gland tissues in diagnosis. Therefore, the radiographic image of the breast (breast image) captured by mammography is processed by, for example, a dedicated operation terminal and is then used for diagnosis by a doctor. The doctor interprets the breast image displayed on, for example, a display to examine whether or not an abnormal part is present.

In contrast, in the mammography, tomosynthesis imaging has been proposed which moves a radiation source, irradiates the breast with radiation from a plurality of radiation source positions to acquire a plurality of projection images, adds the plurality of acquired projection images to generate a tomographic image in which a desired tomographic plane has been highlighted. In the tomosynthesis imaging, the radiation source is moved in parallel to a radiation detector or is moved so as to draw a circular or elliptical arc according to the characteristics of an imaging apparatus and the required tomographic image and imaging is performed for the breast at a plurality of radiation source positions to acquire a plurality of projection images. Then, the projection images are reconstructed using a back projection method, such as a simple back projection method or a filtered back projection method, to generate tomographic images.

The tomographic images are generated in a plurality of tomographic planes of the breast, which makes it possible to separate structures that overlap each other in the depth direction in which the tomographic planes are arranged in the breast. Therefore, it is possible to fine the lesion that has been difficult to detect in a two-dimensional image (hereinafter, referred to as a simple two-dimensional image) acquired by simple imaging according to the related art.

In the above-mentioned tomosynthesis imaging, a region including only the breast in the projection image is important and a region other than the breast is unnecessary for generating a tomographic image. Therefore, a method has been proposed which extracts a region surrounding the breast from a projection image and generates a tomographic image using only the extracted region (see JP2006-519625A).

In mammography, imaging is performed in a state in which the breast is compressed by a compression plate. Therefore, the edge of the compression plate is included as a linear-shaped image in the image acquired by imaging. In addition, in a case in which the edge of the compression plate is bent upward to form a side wall, the side wall is included as a strip-shaped image in the image. Here, in a case in which the breast is compressed by the compression plate, the breast may be spread to the vicinity of the edge of the compression plate, depending on the size of the breast. In this case, an image (hereinafter, referred to as an edge image) caused by the edge and side wall of the compression plate is likely to be included in the breast image included in the projection image. In the tomosynthesis imaging, the image of the breast is captured while the radiation source is moved. In particular, in a case in which the breast is irradiated with radiation in a direction that is inclined with respect to a line perpendicular to a detection surface of the radiation detector, the possibility that the edge image of the compression plate will be included in the projection image increases.

As such, in a case in which reconstruction is performed using the projection image including the edge image, an artifact caused by the edge image is included in the generated tomographic image. The method described in JP2006-519625A extracts the region surrounding the breast in the projection image. Therefore, it is possible to remove the edge image included in a region other than the breast image in the projection image.

However, in a case in which the edge image is superimposed on the breast image in the projection image, it is difficult to remove the edge image using the method described in JP2006-519625A. As a result, an artifact is included in the tomographic image generated by reconstruction.

SUMMARY OF THE INVENTION

The present disclosure has been made in view of the above-mentioned problems and an object of the present disclosure is to reduce the influence of an edge image which is caused by the edge of a compression plate and is included in a projection image acquired by tomosynthesis imaging.

A first image processing apparatus according to the present disclosure comprises: an image acquisition unit that acquires a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; an edge image detection unit that detects an edge image caused by an edge of the compression plate in the plurality of projection images; and a cutout unit that cuts out the projection image according to a positional relationship between the edge image and an image of the object to generate a cut-out projection image.

In the first image processing apparatus according to the present disclosure, the cutout unit may cut out the projection image on the basis of a contour of the object or a contour of the edge image according to the positional relationship between the edge image and the image of the object.

In the first image processing apparatus according to the present disclosure, in a case in which the edge image has a strip shape and the image of the object and the edge image are separated from each other in each of the projection images, the cutout unit may perform a first cutout process of cutting out the projection image on the basis of the contour of the object. In a case in which the image of the object and the edge image come into contact with each other without being superimposed, the cutout unit may perform a second cutout process of cutting out the projection image on the basis of the contour of the object. In a case in which a contour of the image of the object at a position closest to a side edge of the projection image is superimposed on the edge image, the cutout unit may perform a third cutout process of cutting out the projection image on the basis of a contour of the edge image which is superimposed on the image of the object. In a case in which the image of the object and the edge image are superimposed on each other and the image of the object is present on both sides of the edge image, the cutout unit may perform a fourth cutout process of cutting out the projection image on the basis of a contour of the edge image which is far from the contour of the image of the object at the position closest to the side edge of the projection image.

The first image processing apparatus according to the present disclosure may further comprise an interpolation unit that interpolates a region of the image of the object which has been lost by the third cutout process or the fourth cutout process in the cut-out projection image generated by the third cutout process or the fourth cutout process on the basis of at least one of the plurality of projection images.

In the first image processing apparatus according to the present disclosure, in a case in which the edge image has a linear shape and the image of the object and the edge image are separated from each other in each of the projection images, the cutout unit may perform a fifth cutout process of cutting out the projection image on the basis of the contour of the object. In a case in which the image of the object and the edge image come into contact with each other, the cutout unit may perform a sixth cutout process of cutting out the projection image on the basis of the contour of the object. In a case in which the image of the object and the edge image are superimposed on each other, the cutout unit may perform a seventh cutout process of cutting out the projection image on the basis of the edge image.

A second image processing apparatus according to the present disclosure comprises: an image acquisition unit that acquires a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; an edge image detection unit that detects an edge image caused by an edge of the compression plate in the plurality of projection images; a cutout unit that cuts out the projection image on the basis of a contour of the object in each of the projection images to generate a cut-out projection image; and a deletion unit that deletes the edge image in a case in which the edge image is included in the cut-out projection image.

The second image processing apparatus according to the present disclosure may further comprise an interpolation unit that interpolates a region of an image of the object which has been lost by the deletion of the edge image in the cut-out projection image obtained by deleting the edge image, on the basis of at least one of the plurality of projection images.

In the first and second image processing apparatuses according to the present disclosure, in a case in which the compression plate has a rectangular shape and the radiation source is relatively moved in a direction intersecting a set of opposite edges of the compression plate, the edge image detection unit may detect at least the edge image caused by the set of edges of the compression plate.

The term "at least" includes a case in which an edge image caused by a set of sides of the compression plate is detected and a case in which an edge image caused by edges other than the set of edges is detected in addition to the above.

Further, the first and second image processing apparatuses according to the present disclosure may further comprise a display control unit that registers the plurality of cut-out projection images on the basis of a common reference position in the plurality of projection images and displays the plurality of cut-out projection images on a display unit.

The first and second image processing apparatuses according to the present disclosure may further comprise a reconstruction unit that reconstructs the cut-out projection images to generate tomographic images in each of a plurality of tomographic planes of the object.

Further, in the first and second image processing apparatuses according to the present disclosure, the object may be a breast.

A first image processing method according to the present disclosure comprises: acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; detecting an edge image caused by an edge of the compression plate in the plurality of projection images; and cutting out the projection image according to a positional relationship between the edge image and an image of the object to generate a cut-out projection image.

A second image processing method according to the present disclosure comprises: acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; detecting an edge image caused by an edge of the compression plate in the plurality of projection images; cutting out the projection image on the basis of an edge of the object in each of the projection images to generate a cut-out projection image; and deleting the edge image in a case in which the edge image is included in the cut-out projection image.

In addition, programs that cause a computer to perform the first and second image processing methods according to the present disclosure may be provided.

A third image processing apparatus according to the present disclosure comprises a memory that stores commands to be executed by a computer and a processor that is configured to execute the stored commands. The processor performs: a process of acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; a process of detecting an edge image caused by an edge of the compression plate in the plurality of projection images; and a process of cutting out the projection image according to a positional relationship between the edge image and an image of the object to generate a cut-out projection image.

A fourth image processing apparatus according to the present disclosure comprises a memory that stores commands to be executed by a computer and a processor that is configured to execute the stored commands. The processor performs: a process of acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source; a process of detecting an edge image caused by an edge of the compression plate in the plurality of projection images; a process of cutting out the projection image on the basis of an edge of the object in each of the projection images to generate a cut-out projection image; and a process of deleting the edge image in a case in which the edge image is included in the cut-out projection image.

According to the present disclosure, it is possible to generate a tomographic image with reduced artifacts.

DETAILED DESCRIPTION

Figure 1:
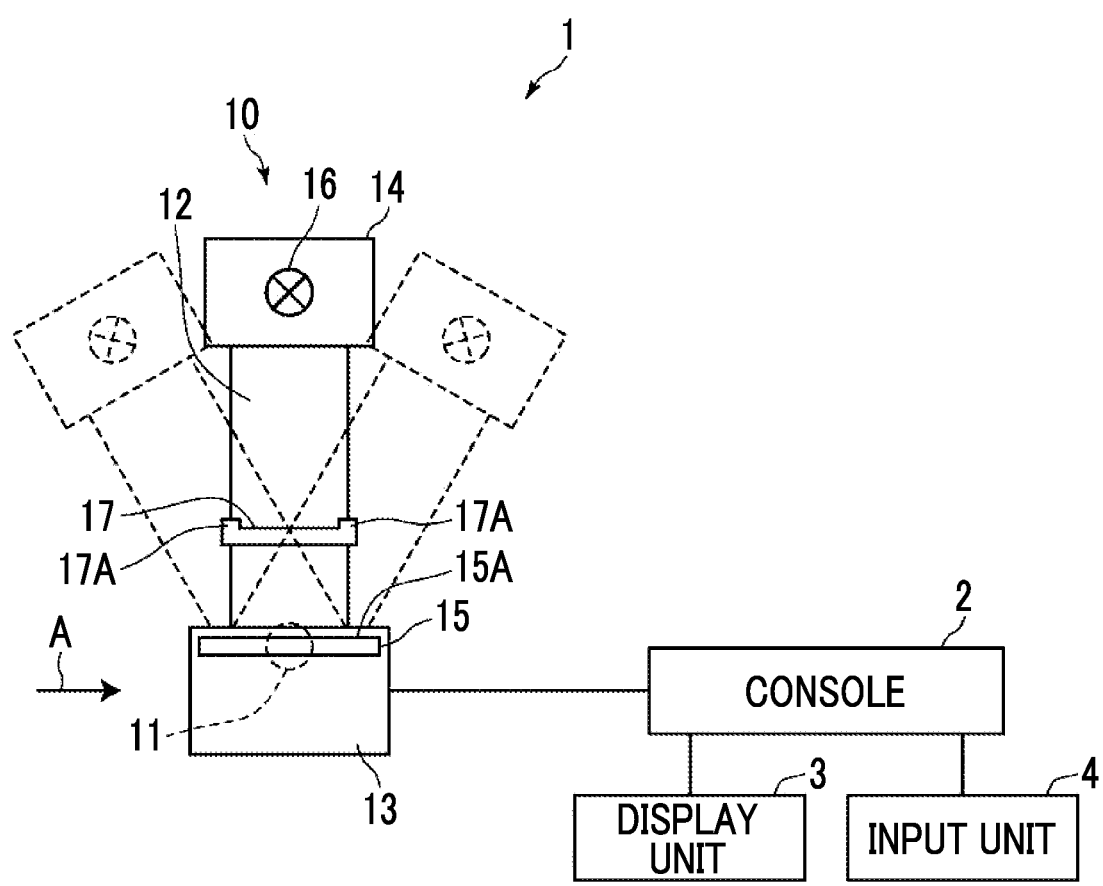
FIG. 1 is a diagram schematically illustrating the configuration of a radiography system to which an image processing apparatus according to a first embodiment of the present disclosure is applied.
Figure 2:
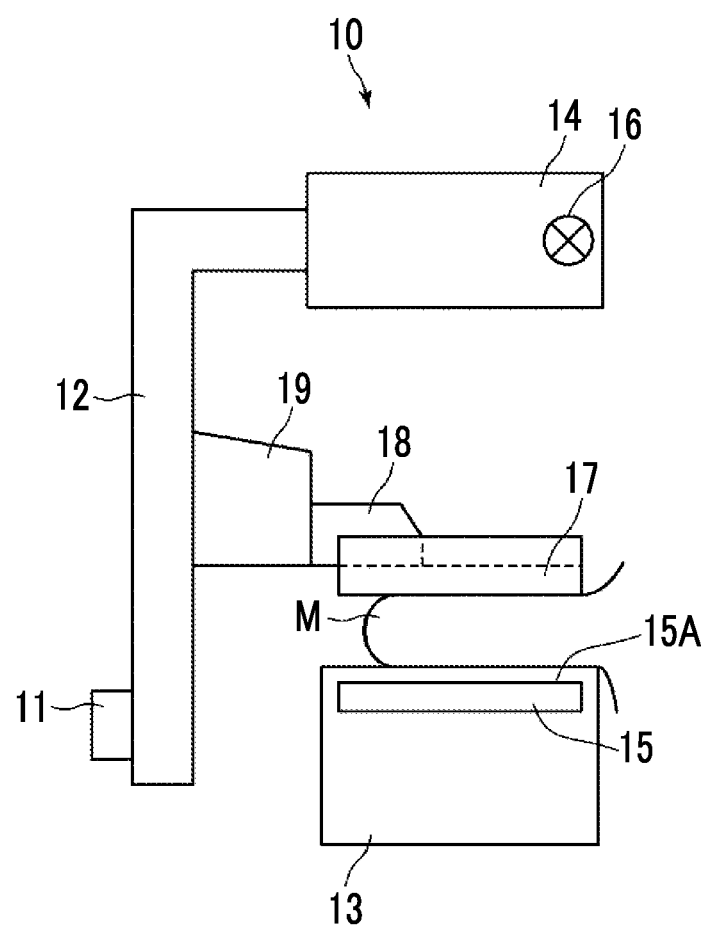
FIG. 2 is a diagram illustrating a mammography apparatus as viewed from the direction of an arrow A in FIG. 1.

Hereinafter, embodiments of the present disclosure will be described with reference to the drawings. FIG. 1 is a diagram schematically illustrating the configuration of a radiography system to which an image processing apparatus according to an embodiment of the present disclosure is applied and FIG. 2 is a diagram illustrating a mammography apparatus included in the radiography system as viewed from the direction of an arrow A in FIG. 1.

As illustrated in FIG. 1, a radiography system 1 according to this embodiment includes a console 2 and a mammography apparatus 10. The console 2 comprises a display unit 3 and an input unit 4.

The radiography system 1 according to this embodiment has a function of capturing an image of the breast using the mammography apparatus 10 and acquiring a breast image which is a radiographic image of the breast on the basis of a command (imaging order) input from an external system (for example, a radiology information system (RIS)) through the console 2 in response to an operation of an operator such as a doctor or a radiology technician. In this embodiment, the mammography apparatus 10 can perform both tomosynthesis imaging and simple imaging in various imaging directions to generate a tomographic image of the breast and a two-dimensional breast image. The two-dimensional breast image means a breast image acquired by the simple imaging.

The mammography apparatus 10 comprises an arm portion 12 that is connected to a base (not illustrated) by a rotation shaft 11. An imaging table 13 is attached to one end of the arm portion 12 and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed and only the radiation emitting unit 14 can be rotated. The rotation of the arm portion 12 is controlled by the console 2.

A radiation detector 15, such a flat panel detector, is provided in the imaging table 13. The radiation detector 15 has a radiation detection surface 15A. For example, a circuit substrate including a charge amplifier that converts a charge signal read from the radiation detector 15 into a voltage signal, a correlated double sampling circuit that samples the voltage signal output from the charge amplifier, and an analog-to-digital (AD) conversion unit that converts the voltage signal into a digital signal is also provided in the imaging table 13. In this embodiment, the radiation detector 15 is used. However, the invention is not limited to the radiation detector 15 and any unit may be used as long as it can detect radiation and convert the radiation into an image.

The radiation detector 15 can repeatedly perform the recording and reading of a radiographic image. A so-called direct-type radiation detector that directly converts radiation, such as X-rays, into charge may be used or a so-called indirect-type radiation detector that converts radiation into visible light and converts the visible light into a charge signal may be used. As a method for reading a radiographic image signal, it is desirable to use a so-called TFT reading method that turns on and off a thin film transistor (TFT) switch to read a radiographic image signal or a so-called optical reading method that emits reading light to read a radiographic image signal. However, the invention is not limited thereto and other methods may be used.

A radiation source 16 is provided in the radiation emitting unit 14. The radiation source 16 emits X-rays as radiation. The console 2 controls the timing when radiation is emitted from the radiation source 16 and the radiation generation conditions of the radiation source 16, that is, the selection of materials forming a target and a filter, a tube voltage, an irradiation time, and the like.

Further, the arm portion 12 is provided with a compression plate 17 that presses a breast M to compress the breast M, a support portion 18 that supports the compression plate 17, and a movement mechanism 19 that moves the support portion 18 in the up-down direction of FIGS. 1 and 2. A gap between the compression plate 17 and the imaging table 13, that is, a compression thickness is input to the console 2. The compression plates 17 with a plurality of sizes and shapes corresponding to the types of imaging are prepared. Therefore, the compression plate 17 is attached to the support portion 18 so as to be replaceable. Further, side walls 17A are formed at the left and right edges of the compression plate 17 in FIG. 1. The side walls 17A are formed to reduce the pain of a patient in a case in which the breast M compressed by the compression plate 17 protrudes from the compression plate 17.

The display unit 3 is a display device, such as a cathode ray tube (CRT) or a liquid crystal display, and displays, for example, messages necessary for operations in addition to the breast image, as described below. The display unit 3 may include a speaker that outputs sound.

The input unit 4 is, for example, a keyboard, a mouse, or a touch-panel-type input device and receives the operation of the mammography apparatus 10 by the operator. In addition, the input unit 4 receives the input of various kinds of information, such as imaging conditions, required for performing tomosynthesis imaging and an information correction command. In this embodiment, each unit of the mammography apparatus 10 is operated according to the information input from the input unit 4 by the operator.

An image processing program according to the first embodiment is installed in the console 2. In this embodiment, the console 2 may be a workstation or a personal computer that is directly operated by the operator or may be a server computer that is connected to them through a network. The image processing program is stored in a storage device of the server computer connected to the network or a network storage so as to be accessed from the outside. The image processing program is downloaded and installed in the computer as required. Alternatively, the image processing program is recorded on a recording medium, such as a digital versatile disc (DVD) or a compact disc read only memory (CD-ROM), is distributed, and is installed in the computer from the recording medium.

Figure 3:
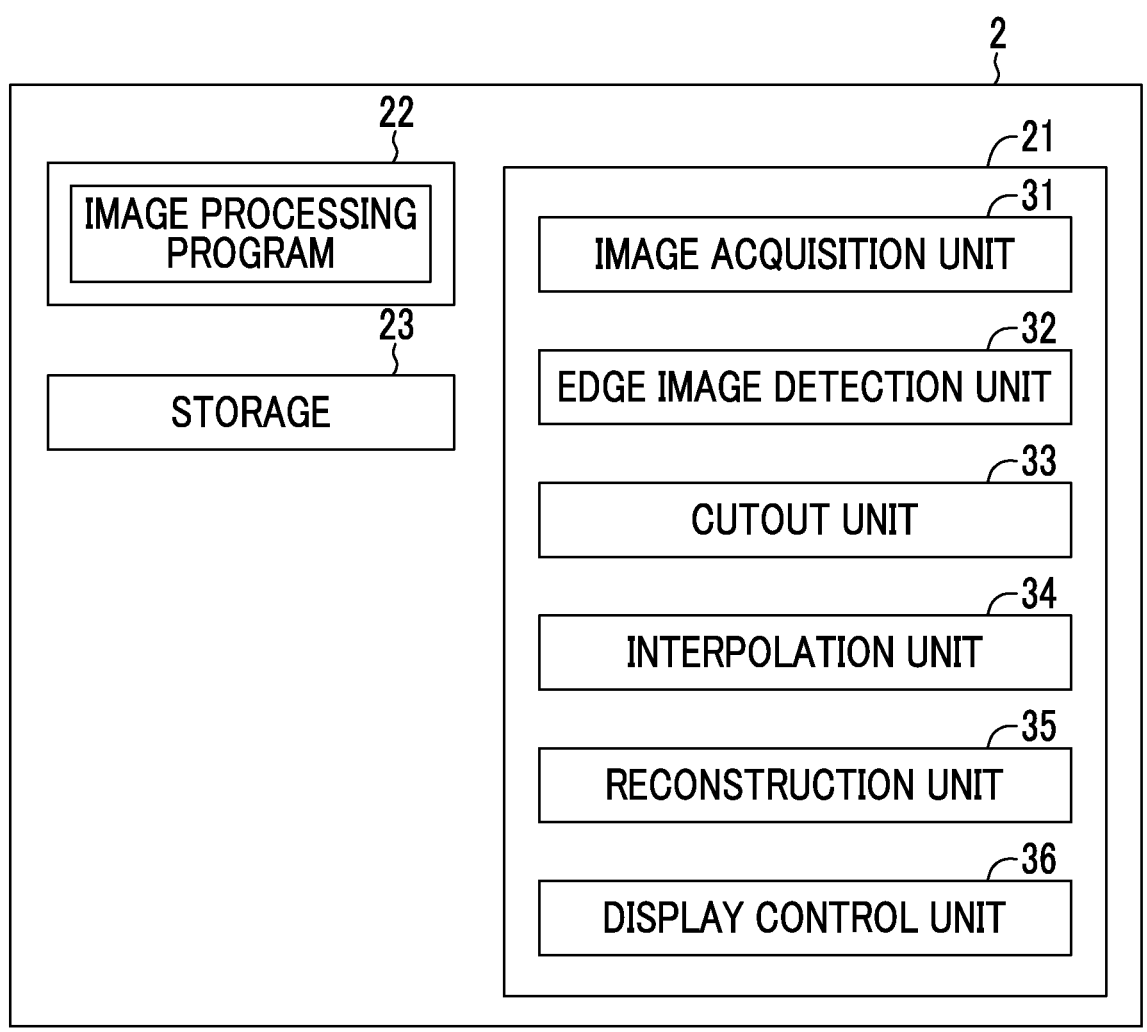
FIG. 3 is a diagram schematically illustrating the configuration of an image processing apparatus implemented by installing an image processing program in a computer forming a console in the first embodiment.

FIG. 3 is a diagram schematically illustrating the configuration of an image processing apparatus implemented by installing the image processing program according to the first embodiment in a computer configuring the console 2. As illustrated in FIG. 3, an image processing apparatus 20 includes a central processing unit (CPU) 21, a memory 22, and a storage 23 as a standard computer configuration.

The storage 23 is a storage device, such as a hard disk drive or a solid state drive (SSD), and stores various kinds of information including a program for driving each unit of the mammography apparatus 10 and the image processing program. In addition, the breast image acquired by imaging is stored in the storage 23.

The memory 22 temporarily stores the programs that have been stored in the storage 23 in order to cause the CPU 21 to execute various processes. The image processing program defines the following processes as the processes executed by the CPU 21: an image acquisition process of directing the mammography apparatus 10 to perform tomosynthesis imaging and acquiring a plurality of projection images of the breast M corresponding to each of a plurality of radiation source positions; an edge image detection process of detecting an edge image caused by the edge of the compression plate 17 in the plurality of projection images; a cutout process of cutting out the projection image according to the positional relationship between the edge image and the image of the breast M to generate a cut-out projection image; an interpolation process of interpolating the breast image lost by the cutout process, which will be described below, in the cut-out projection image; a reconstruction process of reconstructing the plurality of projection images to generate a plurality of tomographic images in each of a plurality of tomographic planes of the breast M which is an object; and a display control process of registering the plurality of projection images and displaying the plurality of projection images on the display unit 3.

Then, the CPU 21 executes these processes according to the image processing program such that the CPU 21 of the console 2 functions as an image acquisition unit 31, an edge image detection unit 32, a cutout unit 33, an interpolation unit 34, a reconstruction unit 35, and a display control unit 36.

Figure 4:
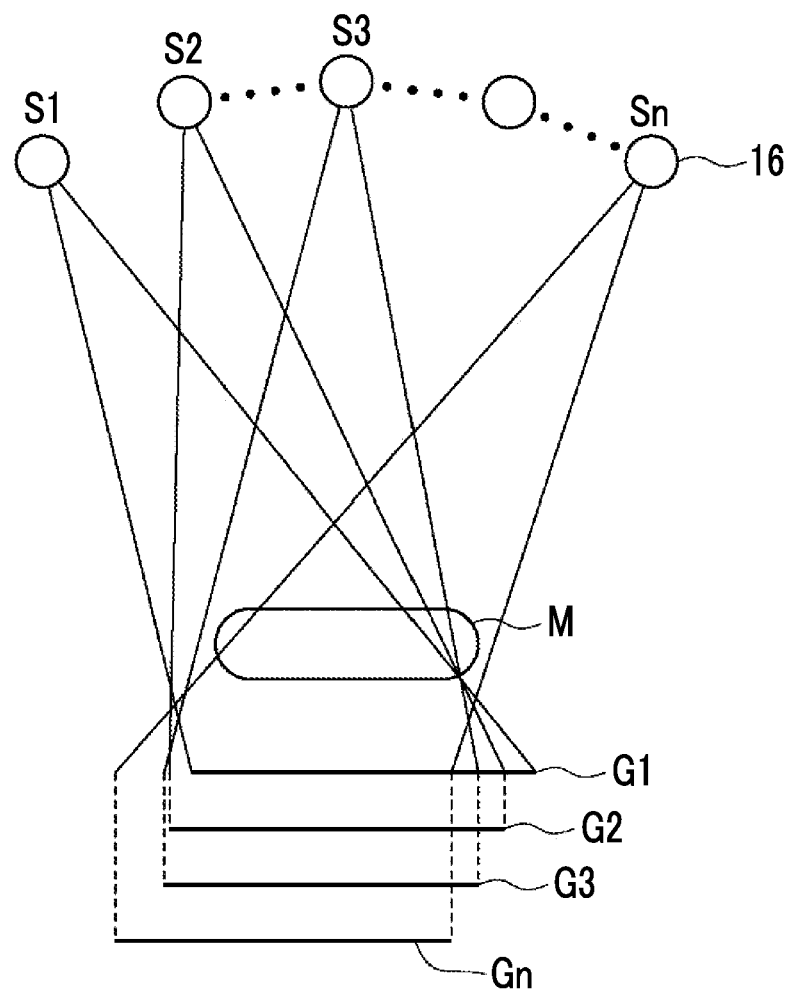
FIG. 4 is a diagram illustrating the acquisition of a projection image.

The image acquisition unit 31 rotates the arm portion 12 around the rotation shaft 11 to move the radiation source 16, irradiates the breast M with radiation at a plurality of radiation source positions caused by the movement of the radiation source 16 under imaging conditions for tomosynthesis imaging, and detects radiation transmitted through the breast M using the radiation detector 15, thereby acquiring a plurality of projection images Gi (i=1 to n, where n is the number of radiation source positions; for example, n=15) at the plurality of radiation source positions. FIG. 4 is a diagram illustrating the acquisition of the projection images Gi. As illustrated in FIG. 4, the radiation source 16 is moved to each of radiation source positions S1, S2, . . . , Sn. The radiation source 16 is driven at each of the radiation source positions to irradiate the breast M with radiation. The radiation detector 15 detects the radiation transmitted through the breast M. In this way, projection images G1, G2, . . . , Gn corresponding to each of the radiation source positions S1 to Sn are acquired. At the radiation source positions S1 to Sn, the same dose of radiation is emitted to the breast M. The plurality of acquired projection images Gi are stored in the storage 23.

Figure 5:
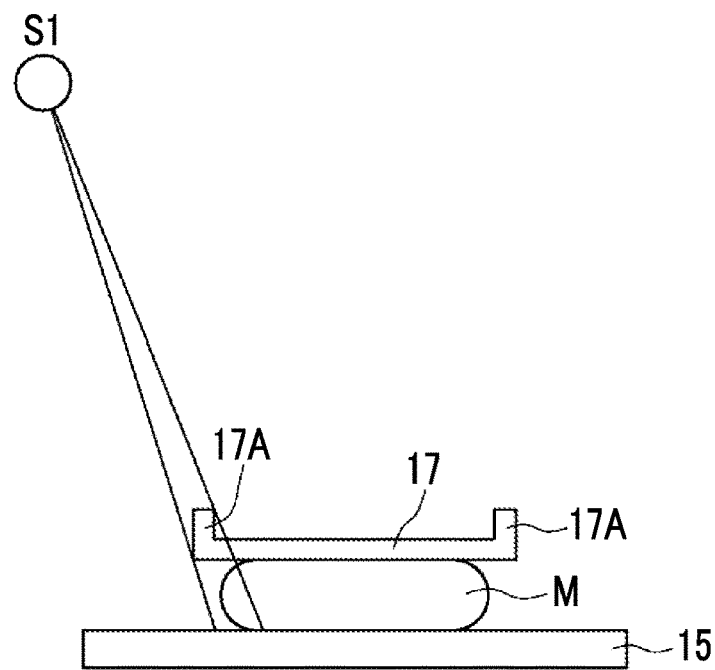
FIG. 5 is a diagram illustrating a geometric relationship among a radiation source, a compression plate, a breast, and a radiation detector.
Figure 6:
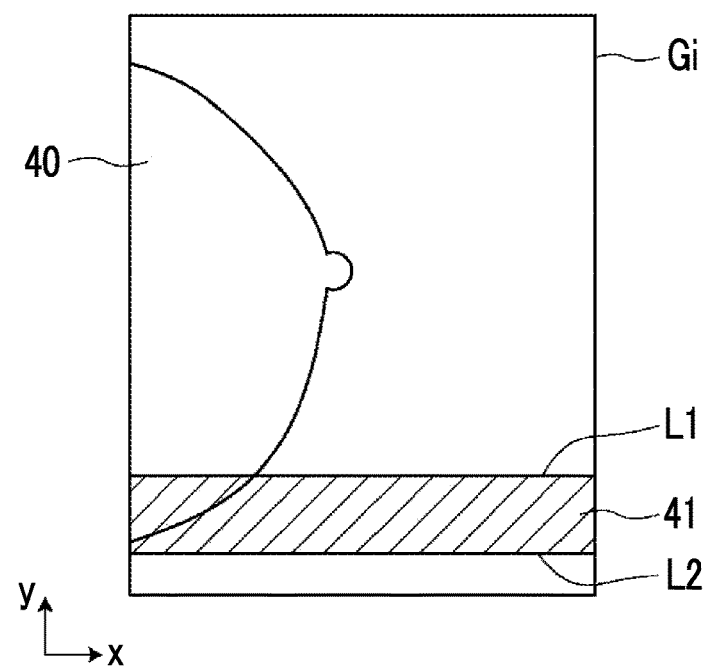
FIG. 6 is a diagram illustrating a projection image including an edge image.

In this embodiment, the side walls 17A are formed at the edge of the compression plate 17. Therefore, in particular, in a case in which the position of the radiation source 16 is inclined with respect to a line perpendicular to the detection surface 15A of the radiation detector 15, radiation transmitted through the side wall 17A is transmitted through the breast M and is detected by the radiation detector 15 as illustrated in FIG. 5. In this case, in the acquired projection image G1, as illustrated in FIG. 6, a strip-shaped image (hereinafter, referred to as an edge image 41) caused by the side wall 17A of the compression plate 17 is superimposed on an image of the breast M (hereinafter, referred to as a breast image 40) included in the projection image Gi. As described above, in a case in which the strip-shaped edge image 41 corresponding to the side wall 17A is included in the projection image Gi, an artifact is included in a tomographic image generated by reconstructing the plurality of projection images Gi as described below. In the following description, it is assumed that, in various images including the projection images Gi, a direction in which a side of the breast image 40 close to the chest wall extends in a state in which the breast image 40 can be visually recognized as illustrated in FIG. 6, that is, the up-down direction is referred as the y direction and the right-left direction orthogonal to the side close to the chest wall is referred to as the x direction.

Therefore, the edge image detection unit 32 detects the edge image 41 caused by the compression plate 17 in the plurality of projection images Gi. Specifically, the edge image detection unit 32 detects a strip-shaped image caused by the side wall 17A as the edge image 41. As illustrated in FIG. 6, the side wall 17A is included as the strip-shaped edge image 41 that extends in the x direction in the projection image Gi. The edge image 41 is surrounded by two straight lines L1 and L2 which extend in the x direction and the contour of the projection image Gi which extends in the y direction.

Here, the size of the compression plate 17 and the height and thickness of the side wall 17A are known. The thickness of the breast M during imaging is the same as the height of the compression plate 17 and is known. In addition, the position of the radiation source 16 where each projection image Gi has been acquired and the position of the detection surface 15A of the radiation detector 15 are known. Therefore, the edge image detection unit 32 stores the information of the size of the compression plate 17, the height of the side wall 17A, and the thickness of the compression plate 17 in the storage 23 and detects the edge image 41 included in the projection image Gi on the basis of the information of the size of the compression plate 17 used, the height of the side wall 17A, and the thickness of the compression plate 17 read from the storage 23 and the geometric positional relationship among the thickness of the breast M during imaging, the position of the radiation source 16 where each projection image Gi has been acquired, and the position of the detection surfaces 15A of the radiation detector 15.

Here, a plurality of types of compression plates 17 that have no side walls 17A or have different sizes and thicknesses are prepared. Therefore, in this embodiment, the type of compression plate 17 may be identified using any method described in, for example, JP2012-235960A and the position of the edge image 41 may be detected geometrically on the basis of, for example, the size and shape of the identified type of compression plate 17 and the presence or absence of the side wall 17A. In the method described in JP2012-235960A, holes corresponding to types are formed in the compression plate 17, identification pins are attached to an attachment portion of the compression plate 17, and the type of compression plate 17 is identified according to the number of identification pins inserted into the holes formed in the compression plate 17. In this case, the height, size, and thickness of the side wall 17A are stored for each type of compression plate 17 in the storage 23. The edge image detection unit 32 reads the information of the height, size, and thickness of the side wall 17A for a specified type of compression plate 17 from the storage 23 and detects the edge image 41 included in the projection image Gi on the basis of the read height, size, and thickness of the side wall 17A and the geometric positional relationship among the thickness of the breast M during imaging, the position of the radiation source 16 where each projection image Gi has been acquired, and the position of the detection surfaces 15A of the radiation detector 15.

The information of the height of the side wall 17A and the size and thickness of the compression plate 17 may be acquired by an input from the operator through the input unit 15.

The edge image detection unit 32 may detect the straight lines L1 and L2 in the projection image Gi using, for example, a differential filter and may detect a region surrounded by the straight lines L1 and L2 and the sides of the projection image Gi which extend in the y direction as the edge image 41 in the projection image Gi. Alternatively, the edge image 41 may be detected using a learned model such as a neural network that has been subjected to machine learning so as to detect the edge image 41.

In this embodiment, as illustrated in FIG. 1, the side walls 17A of the compression plate 17 are provided in a set of edges which face each other in the movement direction of the radiation source 16. Therefore, in some cases, the edge images 41 are included on both the upper and lower sides of the breast image 40 in the projection image Gi illustrated in FIG. 6, depending on the position of the radiation source 16. In this embodiment, it is assumed that the edge image detection unit 32 detects the edge images 41 on both the upper and lower sides of the breast image 40 in the projection image Gi.

The cutout unit 33 cuts out each projection image Gi according to the positional relationship between the edge image 41 detected by the edge image detection unit 32 and the breast image 40 to generate a cut-out projection image. Here, the breast image 40 and the edge image 41 have the following four positional relationships according to the position of the radiation source 16 in a case in which the projection image Gi is acquired.

(1) The breast image 40 and the edge image 41 are separated from each other.

(2) The breast image 40 and the edge image 41 come into contact with each other without being superimposed.

(3) The contour of the breast image 40 at a position closest to a side edge of the projection image Gi is superimposed on the edge image 41.

(4) The breast image 40 and the edge image 41 are superimposed on each other and the breast images 40 is present on both sides of the edge image 41.

Figure 7:
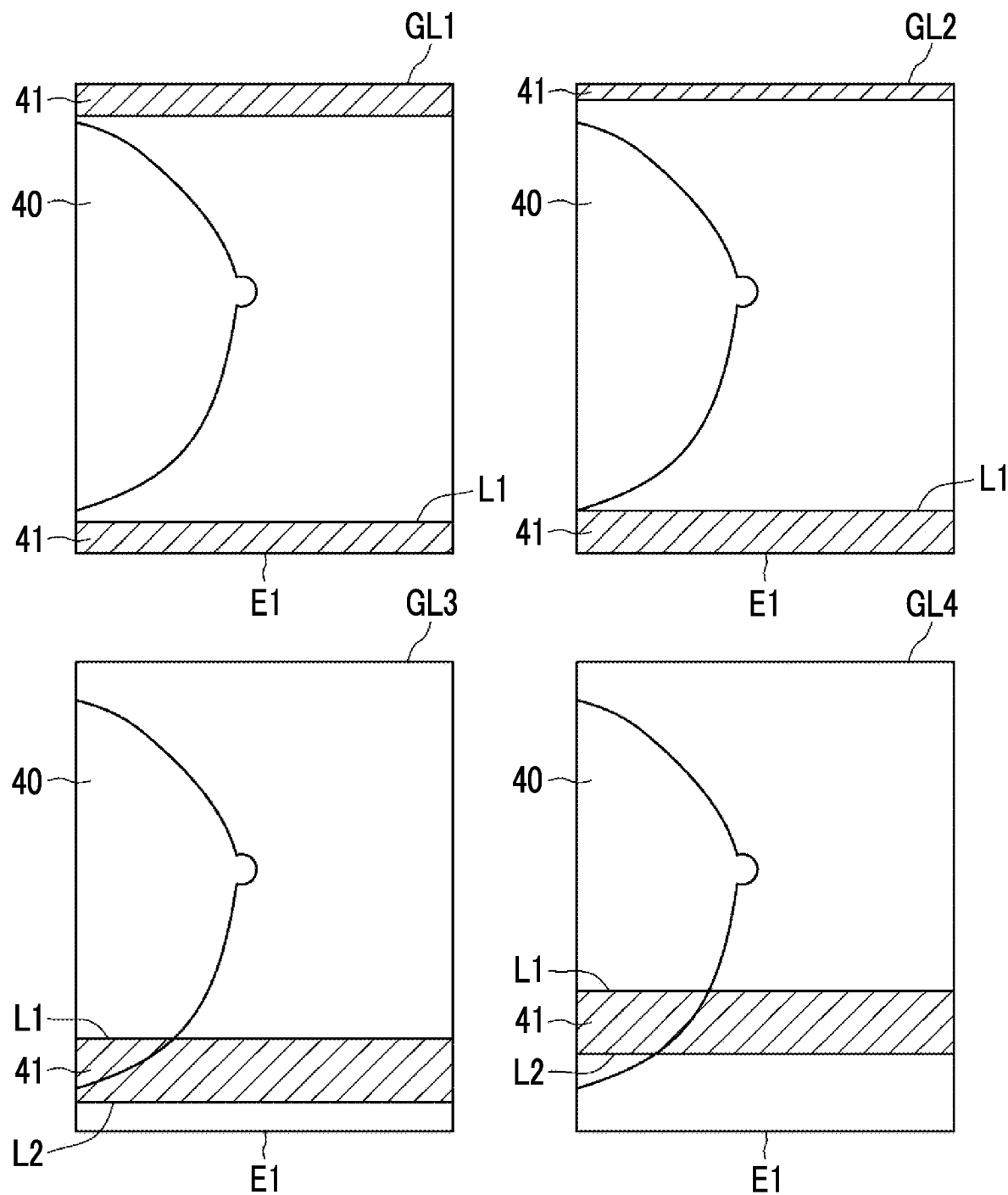
FIG. 7 is a diagram illustrating a positional relationship between an edge image and a breast image in a case in which the edge image has a linear shape in the first embodiment.

"The breast image 40 and the edge image 41 are separated from each other" in the positional relationship (1) means a state in which the breast image 40 and the edge image 41 are not superimposed on each other and a directly-irradiated region obtained by the direct emission of radiation to the radiation detector 15 is present between the breast image 40 and the straight line L1 on the side of the edge image 41 which is close to the breast image 40 as illustrated in a projection image GL1 of FIG. 7. In this case, the edge images 41 are often included in both the upper part and the lower part of the projection image GL1.

"The breast image 40 and the edge image 41 come into contact with each other without being superimposed" in the positional relationship (2) means a state in which the contour of the breast image 40 at the position closest to the lower side E1 of the projection image Gi which extends in the x direction comes into contact with the straight line L1 forming the contour of the edge image 41 as illustrated in a projection image GL2 of FIG. 7. In this case, in the projection image GL2, the width of the lower edge image 41 is large and the width of the upper edge image 41 is small, as compared to the projection image GL1. In the projection image GL2, the upper edge image 41 has the above-described positional relationship (1).

"The contour of the breast image 40 at the position closest to the side edge of the projection image Gi is superimposed on the edge image 41" in the positional relationship (3) means that the contour of the breast image 40 at a position farthest from the position of the nipple of the breast image 40 in the y direction of the projection image Gi is superimposed on the edge image 41. Specifically, as illustrated in a projection image GL3 of FIG. 7, this means a state in which the contour of the breast image 40 at the position closest to the lower side E1 of the projection image GL3 is superimposed on the edge image 41. In addition, the positional relationship (3) includes a state in which the contour of the breast image 40 at the position closest to the lower side E1 of the projection image GL3 comes contact with the straight line L2 of the edge image 41 which is closer to the lower side E1. In this case, in the projection image GL3, the width of the lower edge image 41 is larger than that in the projection image GL2 and the upper edge image 41 is not included in the projection image GL2.

"The breast image 40 and the edge image 41 are superimposed on each other and the breast image 40 is present on both sides of the edge image 41" in the positional relationship (4) means a state in which the contour of the breast image 40 at the position closest to the lower side E1 of a projection image GL4 is closer to the lower side E1 of the projection image GL4 than the straight line L2 of the edge image 41 at the position closest to the lower side E1 of the projection image GL4, as illustrated in a projection image GL4 of FIG. 7.

Figure 8:
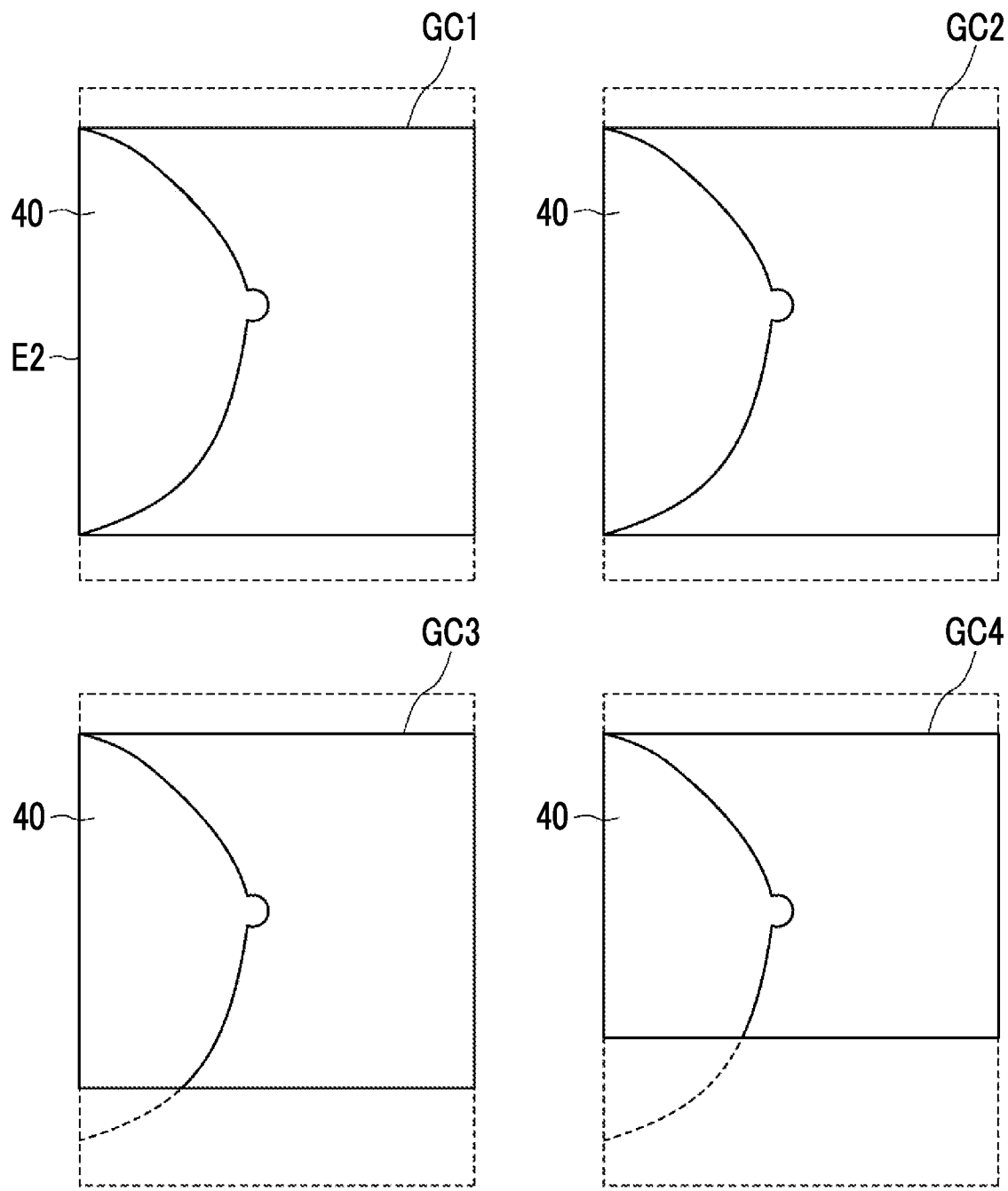
FIG. 8 is a diagram illustrating a cutout process in the first embodiment.

In the case of the positional relationship (1), the cutout unit 33 performs a first cutout process of cutting out the projection image GL1 on the basis of the contour of the breast image 40 to generate a cut-out projection image GC1 illustrated in FIG. 8. That is, the cutout unit 33 cuts out the projection image GL1 along lines that extend in the x direction through intersection points between the contour of the breast image 40 and the left side E2 of the projection image GL1 to generate the cut-out projection image GC1. In the cutout process, the cutout unit 33 determine the positional relationship between the breast image 40 and the edge image 41 at each of the upper and lower positions of the projection image GL1 to perform the cutout process. It is assumed that, in a case in which the edge image 41 is not included at the upper and lower positions of the projection image Gi, the cutout unit 33 performs the first cutout process.

In the case of the positional relationship (2), similarly to the case of the positional relationship (1), the cutout unit 33 performs a second cutout process of cutting out the projection image GL2 on the basis of the contour of the breast image 40 to generate a cut-out projection image GC2 illustrated in FIG. 8. In an upper region of the projection image GL2, the cutout unit 33 performs the first cutout process.

In the case of the positional relationship (3), the cutout unit 33 performs a third cutout process of cutting out the projection image GL3 on the basis of the contour of the edge image 41 which is superimposed on the breast image 40 to generate a cut-out projection image GC3 illustrated in FIG. 8. That is, the projection image GL3 is cut out along the straight line L1 of the edge image 41 to generate the cut-out projection image GC3. In an upper region of the projection image GL3, the cutout unit 33 performs the first cutout process.

In the case of the positional relationship (4), the cutout unit 33 performs a fourth cutout process of cutting out the projection image GL4 on the basis of the contour of the edge image 41 which is far from the contour of the breast image 40 at the position closest to the side edge of the projection image GL4 to generate a cut-out projection image GC4 illustrated in FIG. 8. That is, the projection image GL4 is cut out along the straight line L1 of the edge image 41 to generate the cut-out projection image GC4. In the fourth cutout process, a region below the straight line L1 in the projection image GL4 is deleted. In an upper region of the projection image GL4, the cutout unit 33 performs the first cutout process.

Figure 9:
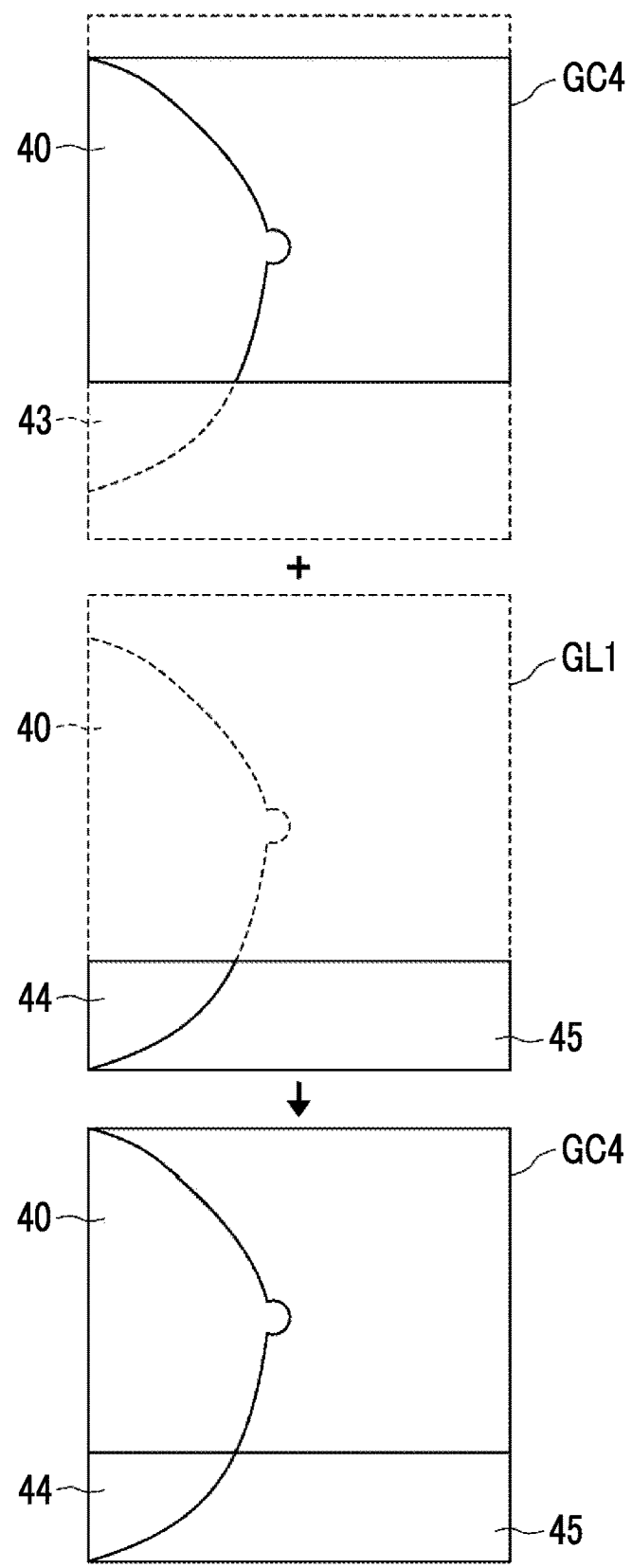
FIG. 9 is a diagram illustrating an interpolation process in the first embodiment.

The interpolation unit 34 interpolates a region of the breast image 40 which has been lost from the projection images GL3 and GL4 by the third cutout process or the fourth cutout process in the cut-out projection image GC3 or GC4 generated by the third cutout process or the fourth cutout process on the basis of at least one of the plurality of projection images Gi. FIG. 9 is a diagram illustrating the interpolation process of the interpolation unit 34. Here, the interpolation process for the cut-out projection image GC4 will be described.

As illustrated in FIG. 9, in the cut-out projection image GC4, a part of a region 43 of the breast image 40 included in the projection image GL4 has been lost by the fourth cutout process. Here, the projection image GL1 includes the breast image 40 of the entire breast M. Therefore, the interpolation unit 34 performs registration between the projection image GL1 and the cut-out projection image GC4 and cuts out a partial image 45 including the breast image (referred to as a lost breast image 44) lost in the cut-out projection image GC4 from the projection image GL1. In this case, the first cutout process is performed for the partial image 45. Then, the cut-out projection image GC4 and the partial image 45 are combined to interpolate a region 43 of the breast image 40 lost by the fourth cutout process in the cut-out projection image GC4. In the following description, the same reference numerals GC3 and GC4 as those used for the cut-out projection images before interpolation are used for the interpolated cut-out projection images.

Figure 10:
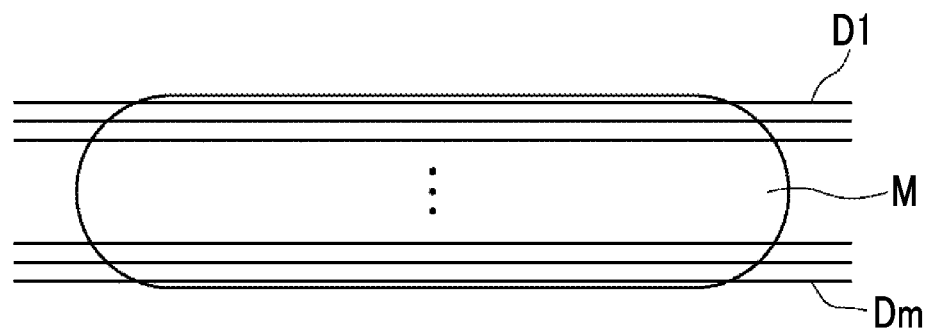
FIG. 10 is a diagram illustrating the generation of a tomographic image.

The reconstruction unit 35 reconstructs the cut-out projection image GCi to generate a tomographic image in which a desired tomographic plane of the breast M has been highlighted. Specifically, the reconstruction unit 35 reconstructs a plurality of cut-out projection images GCi using a known back projection method, such as a simple back projection method or a filtered back projection method, to generate a plurality of tomographic images Dj (j=1 to m) in each of a plurality of tomographic planes of the breast M as illustrated in FIG. 10. At this time, a three-dimensional coordinate position in a three-dimensional space including the breast M is set and pixel values at corresponding pixel positions in the plurality of projection images Gi are reconstructed with respect to the set three-dimensional coordinate position. Then, a pixel value at the coordinate position is calculated.

Figure 11:
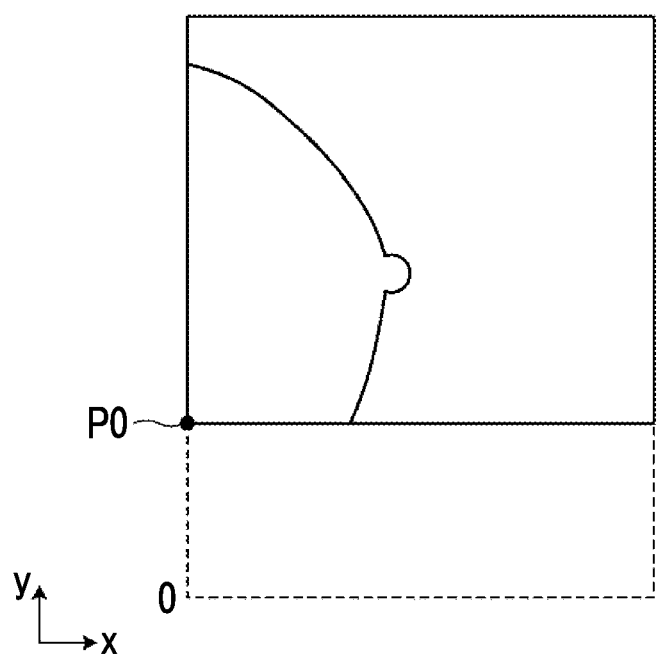
FIG. 11 is a diagram illustrating registration.

The display control unit 36 displays the cut-out projection images GCi. In this embodiment, the cut-out projection images GCi generated by the cutout unit 33 have different sizes depending on the position of the included edge image 41. Therefore, in a case in which the cut-out projection images GCi are displayed in order without any change, the position of the breast image 40 moves up and down in each image on the display unit 3. Therefore, the displayed projection image is difficult to see. In this embodiment, the display control unit 36 registers the cut-out projection images GCi on the basis of a common reference position. In this embodiment, for registration, it is assumed that, in a case in which the cut-out projection image GCi is generated, the cutout unit 33 gives the size of the projection image Gi before cutout and a cutout position to the cut-out projection image Gi as accessory information. As illustrated in FIG. 11, in a case in which the size of the projection image Gi before cutout and the y coordinate of a cutout position P0 are known, the coordinates of the lower left corner of the projection image Gi before cutout can be calculated as an origin O.

Therefore, the display control unit 36 calculates the coordinates of the lower left corner of the projection image Gi before cutout as the origin O with reference to the accessory information given to each cut-out projection image GCi. Then, a plurality of cut-out projection images GCi are displayed such that the positions of the origins O are aligned with each other. Therefore, in the displayed cut-out projection images GCi, the positional deviation between the breast images 40 is not seen. In addition, in each cut-out projection image GCi, the position of the breast image 40 is changed due to a change in the position of the radiation source 16.

Figure 12:
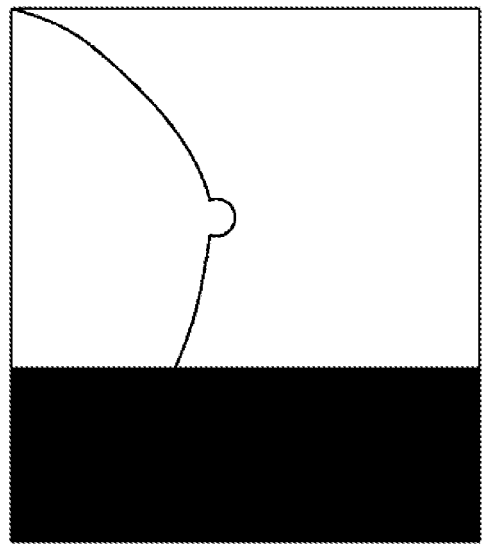
FIG. 12 is a diagram illustrating registration.

In this embodiment, in some cases, the interpolation unit 34 does not perform the interpolation process, which will be described below. In this case, the cut-out projection images GCi have different sizes. In this case, the display control unit 36 may change the sizes of the cut-out projection images other than the cut-out projection image with the largest size so as to be equal to the size of the cut-out projection image with the largest size. The size may be changed by giving a black strip to the other cut-out projection images as illustrated in FIG. 12. In this case, the display control unit 36 may set the position of the lower left corner of the projection image Gi before cutout as the origin O in each of the cut-out projection images GCi with the black strip and may display a plurality of cut-out projection images GCi such that the positions of the origins O are aligned with each other in the same manner as described above.

In addition, the display control unit 36 may set a reference point in each of the cut-out projection images GCi and display the cut-out projection images GCi on the display unit 3 such that the reference points are aligned with each other.

Figure 13:
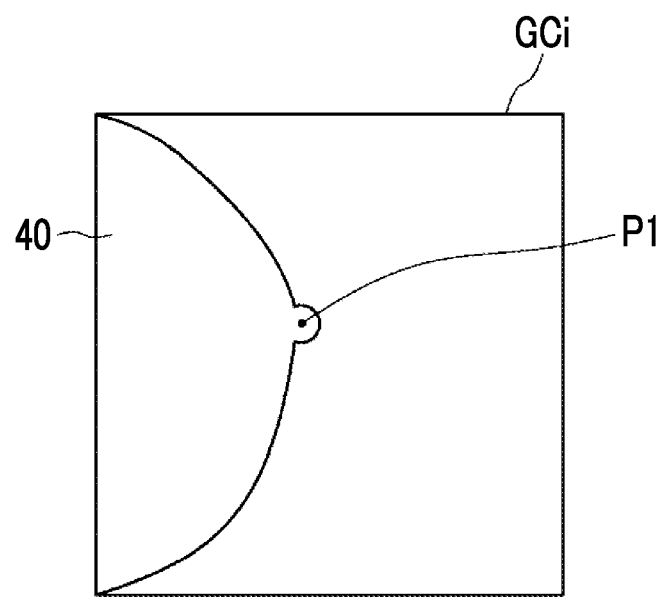
FIG. 13 is a diagram illustrating registration.

As the reference point, for example, the position P1 of the center of gravity of the nipple of the breast image 40 may be used as illustrated in FIG. 13. However, the invention is not limited thereto.

Further, a radiographic image of the breast of the same patient which was captured in the past may be acquired from an image server (not illustrated) and the cut-out projection image GCi may be displayed on the display unit 3 so as to be registered with respect to the acquired radiographic image.

Figure 14:
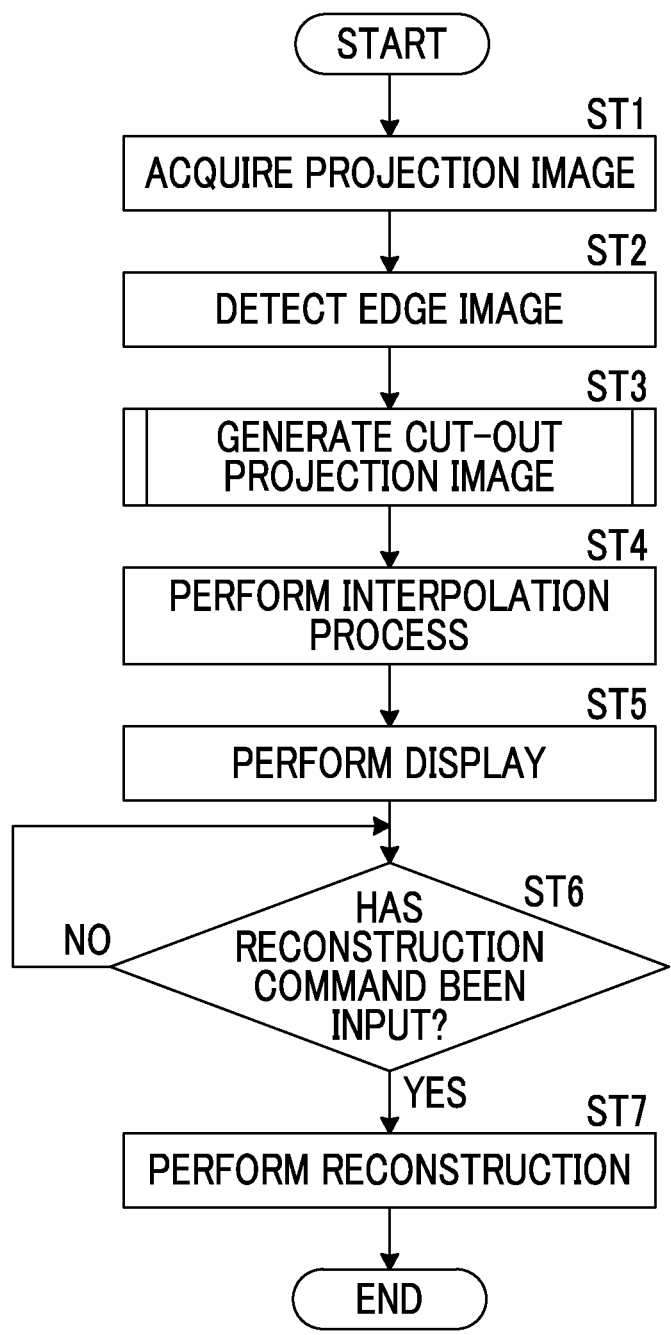
FIG. 14 is a flowchart illustrating a process performed in the first embodiment.

Next, a process performed in this embodiment will be described. FIG. 14 is a flowchart illustrating the process performed in this embodiment. It is assumed that the positioning of the breast M on the imaging table 13 has been completed. The process is started by the input of a tomosynthesis imaging command by the operator through the input unit 4 and the image acquisition unit 31 directs the mammography apparatus 10 to perform tomosynthesis imaging to acquire the projection images Gi (Step ST1). Next, the edge image detection unit 32 detects the edge image 41 caused by the compression plate 17 in a plurality of projection images Gi (Step ST2). Then, the cutout unit 33 cuts out each of the projection images Gi according to the positional relationship between the edge image 41 and the breast image 40 detected by the edge image detection unit 32 to generate the cut-out projection images GCi (Step ST3).

Figure 15:
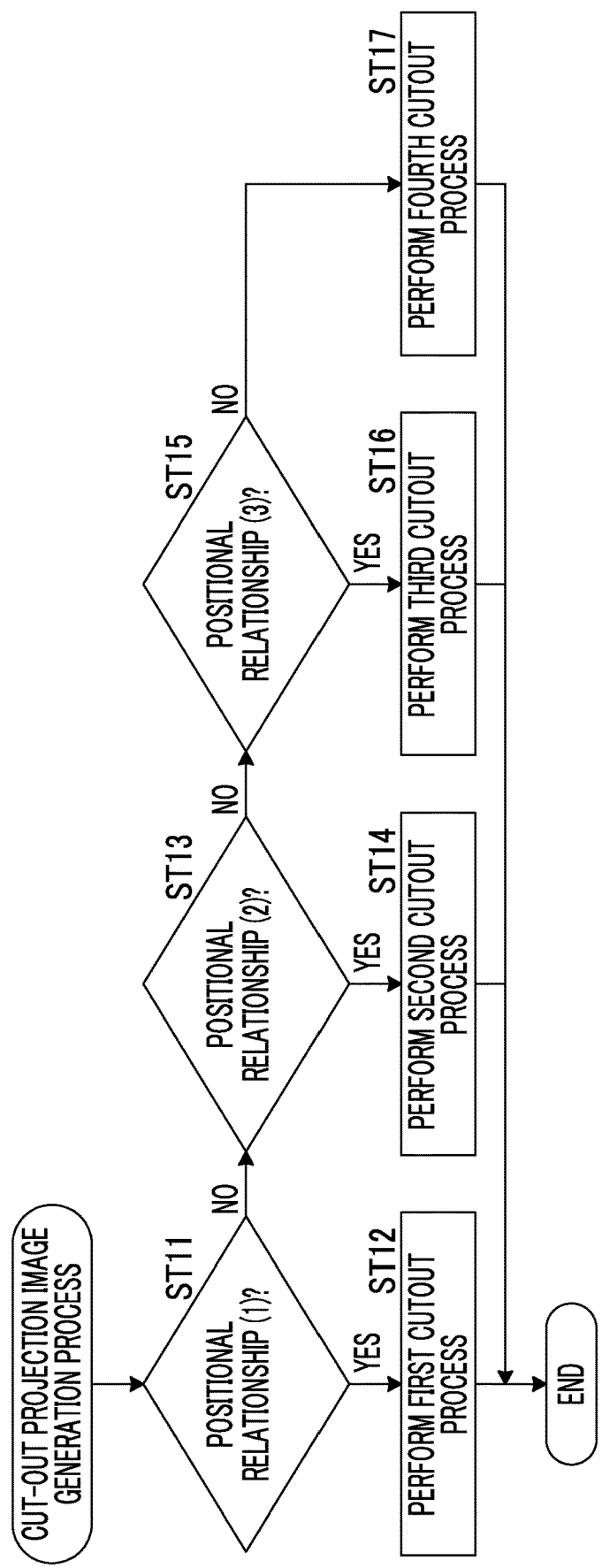
FIG. 15 is a flowchart illustrating a cutout process.

FIG. 15 is a flowchart illustrating a cut-out projection image generation process. The process of the flowchart illustrated in FIG. 15 is performed for each projection image Gi. First, the cutout unit 33 determines whether or not the breast image 40 and the edge image 41 have the positional relationship (1) in the projection image Gi (Step ST11). In a case in which the determination result in Step ST11 is "Yes", the cutout unit 33 performs the first cutout process (Step ST12). Then, the process ends. In a case in which the determination result in Step ST11 is "No", the cutout unit 33 determines whether or not the breast image 40 and the edge image 41 have the positional relationship (2) (Step ST13). In a case in which the determination result in Step ST13 is "Yes", the cutout unit 33 performs the second cutout process (Step ST14).

In a case in which the determination result in Step ST13 is "No", the cutout unit 33 determines whether or not the breast image 40 and the edge image 41 have the positional relationship (3) (Step ST15). In a case in which the determination result in Step ST15 is "Yes", the cutout unit 33 performs the third cutout process (Step ST16). In a case in which the determination result in Step ST15 is "No", the cutout unit 33 performs the fourth cutout process since the breast image 40 and the edge image 41 have the positional relationship (4) (Step ST17). Then, the process ends.

Returning to FIG. 14, the interpolation unit 34 interpolates a region of the breast image 40 which has been lost by the third cutout process or the fourth cutout process in the cut-out projection image generated by the third cutout process or the fourth cutout process on the basis of at least one of the plurality of projection images Gi (an interpolation process, Step ST4).

Then, the display control unit 36 displays the cut-out projection images GCi while registering the cut-out projection images GCi (Step ST5). Further, monitoring whether or not a reconstruction command has been input by the operator through the input unit 4 is started (Step ST6). In a case in which the monitoring result in Step ST6 is "Yes", the reconstruction unit 35 reconstructs the cut-out projection images GCi to generate a plurality of tomographic images (Step ST7). Then, the process ends. The tomographic images generated by the reconstruction are transmitted to the image server (not illustrated) and then stored therein. Alternatively, the tomographic images are displayed on the display unit 3 by the display control unit 36.

As described above, in this embodiment, the edge image 41 caused by the compression plate 17 is detected in a plurality of projection images Gi acquired by tomosynthesis imaging and the projection image Gi is cut out according to the positional relationship between the edge image 41 and the breast image 40 to generate the cut-out projection image GCi. Therefore, it is possible to reduce the influence of the edge image 41 caused by the edge of the compression plate 17 in the cut-out projection image GCi. Then, the cut-out projection image GCi is used to generate a tomographic image with reduced artifacts.

In the first embodiment, since imaging is performed using the compression plate 17 having the side wall 17A, the projection image Gi includes the strip-shaped edge image 41. In contrast, in a case in which imaging is performed using the compression plate 17 without the side wall 17A, the edge image included in the projection image Gi may have a strip shape or a linear shape according to the thickness of the compression plate 17. Hereinafter, a process in a case in which a linear-shaped edge image is included in the projection image Gi will be described as a second embodiment. In addition, even in a case in which the edge image has a linear shape, the edge image has a certain width in the projection image Gi. In this embodiment, for example, in a case in which the width of the edge image is equal to or less than the width of the contour of the breast image 40, the edge image is determined to have a linear shape. In a case in which the width of the edge image is greater than the width of the contour of the breast image 40, the edge image is determined to have a strip shape. However, the invention is not limited thereto.

Figure 16:
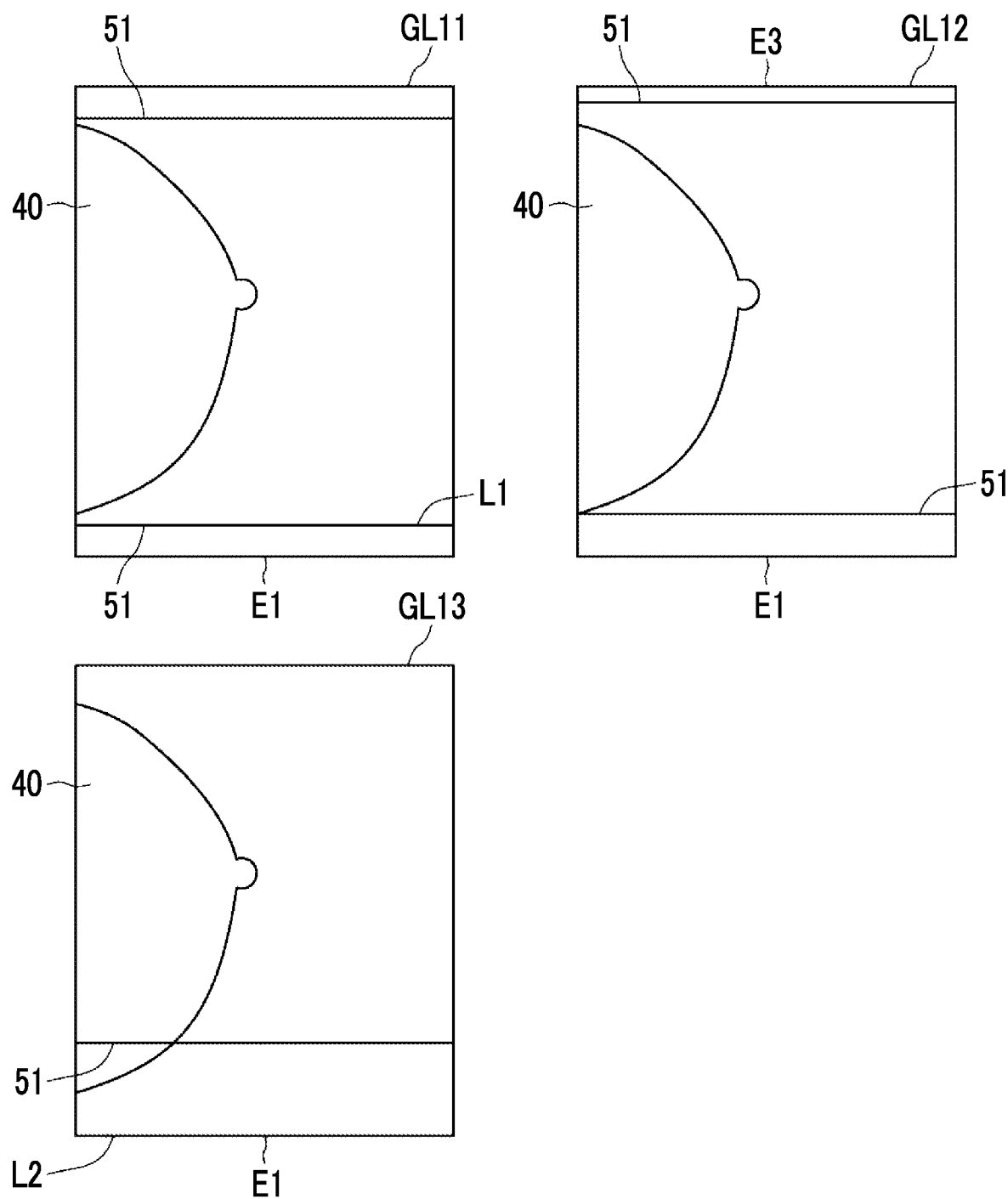
FIG. 16 is a diagram illustrating a positional relationship between an edge image and a breast image in a case in which the edge image has a linear shape in a second embodiment.

FIG. 16 is a diagram illustrating the positional relationship between an edge image and a breast image in a case in which the edge image has a linear shape. As illustrated in FIG. 16, in a case in which an edge image 51 included in the projection image Gi has a linear shape, the breast image 40 and the edge image 51 have the following three positional relationships according to the position of the radiation source 16 in the acquisition of the projection image Gi.

(5) The breast image 40 and the edge image 51 are separated from each other.

(6) The breast image 40 and the edge image 51 come into contact with each other without being superimposed.

(7) The breast image 40 and the edge image 51 are superimposed on each other.

"The breast image 40 and the edge image 51 are separated from each other" in the positional relationship (5) means a state in which the breast image 40 and the edge image 51 are not superimposed on each other and a directly-irradiated region obtained by the direct emission of radiation to the radiation detector 15 is present between the breast image 40 and the edge image 51 as illustrated in a projection image GL11 of FIG. 16. In this case, the edge image 51 is often included in both the upper and lower parts of the projection image GL11.

"The breast image 40 and the edge image 51 come into contact with each other without being superimposed" in the positional relationship (6) means a state in which the contour of the breast image 40 at a position closest to the lower side E1 of a projection image GL12 extending in the x direction comes into contact with the edge image 51 as illustrated in the projection image GL12 of FIG. 16. In this case, in the projection image GL12, the upper edge image 51 is closer to the upper side E3 of the projection image GL12. In the projection image GL12, the upper edge image 51 has the positional relationship (5).

"The breast image 40 and the edge image 51 are superimposed on each other" in the positional relationship (7) means a state in which the contour of the breast image 40 at the position closest to the lower side E1 of a projection image GL13 is closer to the lower side E1 of the projection image GL13 than the edge image 51 as illustrated in the projection image GL13 in FIG. 16.

Figure 17:
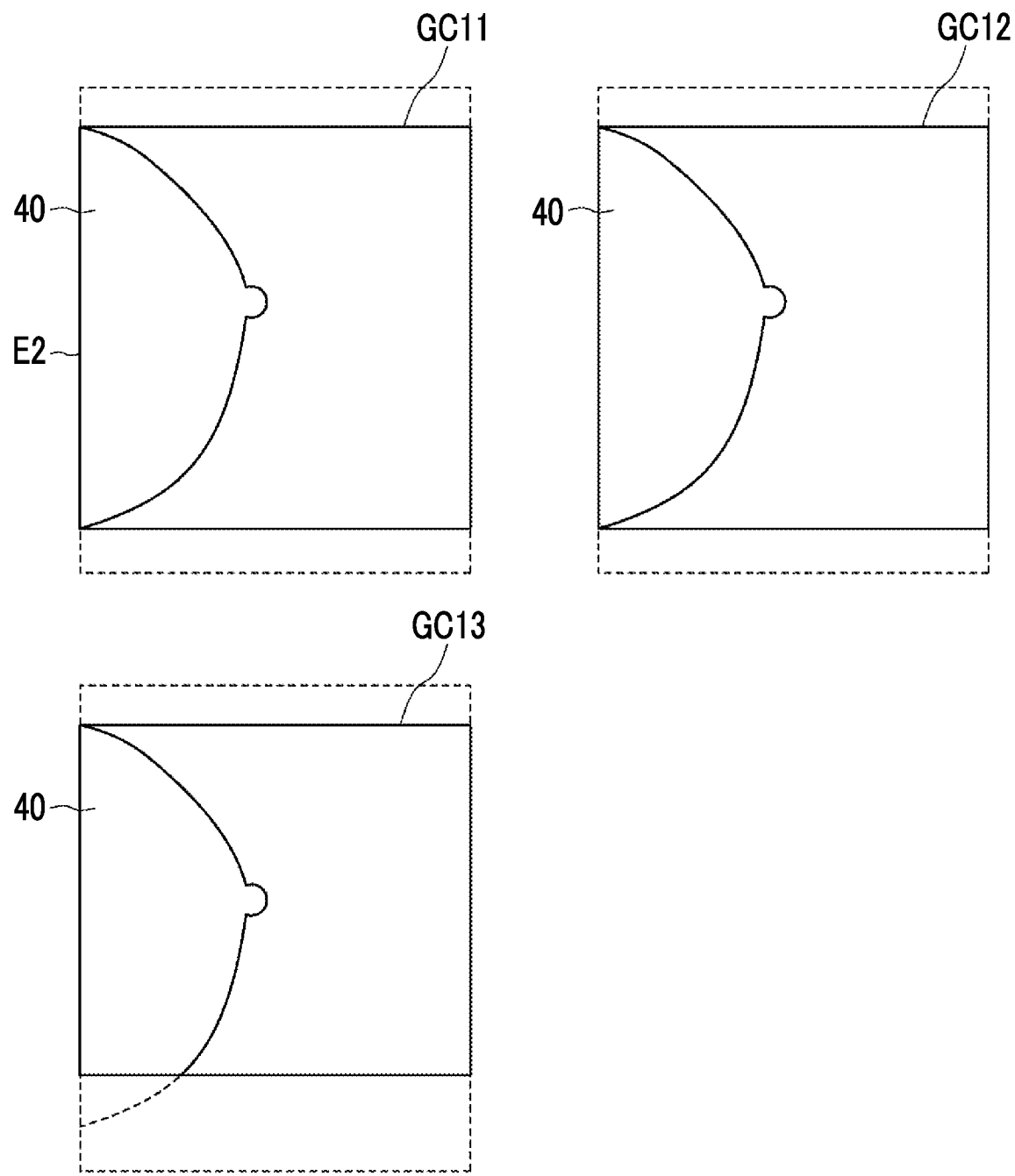
FIG. 17 is a diagram illustrating a cutout process in the second embodiment.

In the second embodiment, in the case of the positional relationship (5), the cutout unit 33 performs a fifth cutout process of cutting out the projection image GL11 on the basis of the contour of the breast image 40 to generate a cut-out projection image GC11 illustrated in FIG. 17. That is, similarly to the first cutout process in the first embodiment, the cutout unit 33 cuts out the projection image GL11 along lines that extend in the x direction through intersection points between the contour of the breast image 40 and the left side E2 of the projection image GL11 to generate a cut-out projection image GC11. In the cutout process, the cutout unit 33 determine the positional relationship between the breast image 40 and the edge image 51 at each of the upper and lower positions of the projection image Gi to perform the cutout process. It is assumed that, in a case in which the edge image 51 is not included at the upper and lower positions of the projection image Gi, the cutout unit 33 performs the fifth cutout process.

In the case of the positional relationship (6), similarly to the case of the positional relationship (5), the cutout unit 33 performs a sixth cutout process of cutting out the projection image GL12 on the basis of the contour of the breast image 40 to generate a cut-out projection image GC12 illustrated in FIG. 17. Here, the fifth cutout process and the sixth cutout process are the same process. In an upper region of the projection image GL12, the cutout unit 33 performs the fifth cutout process.

In the case of the positional relationship (7), the cutout unit 33 performs a seventh cutout process of cutting out the projection image GL13 on the basis of the edge image 51 to generate a cut-out projection image GC13 illustrated in FIG. 17. In an upper region of the projection image GL13, the cutout unit 33 performs the fifth cutout process.

Figure 18:
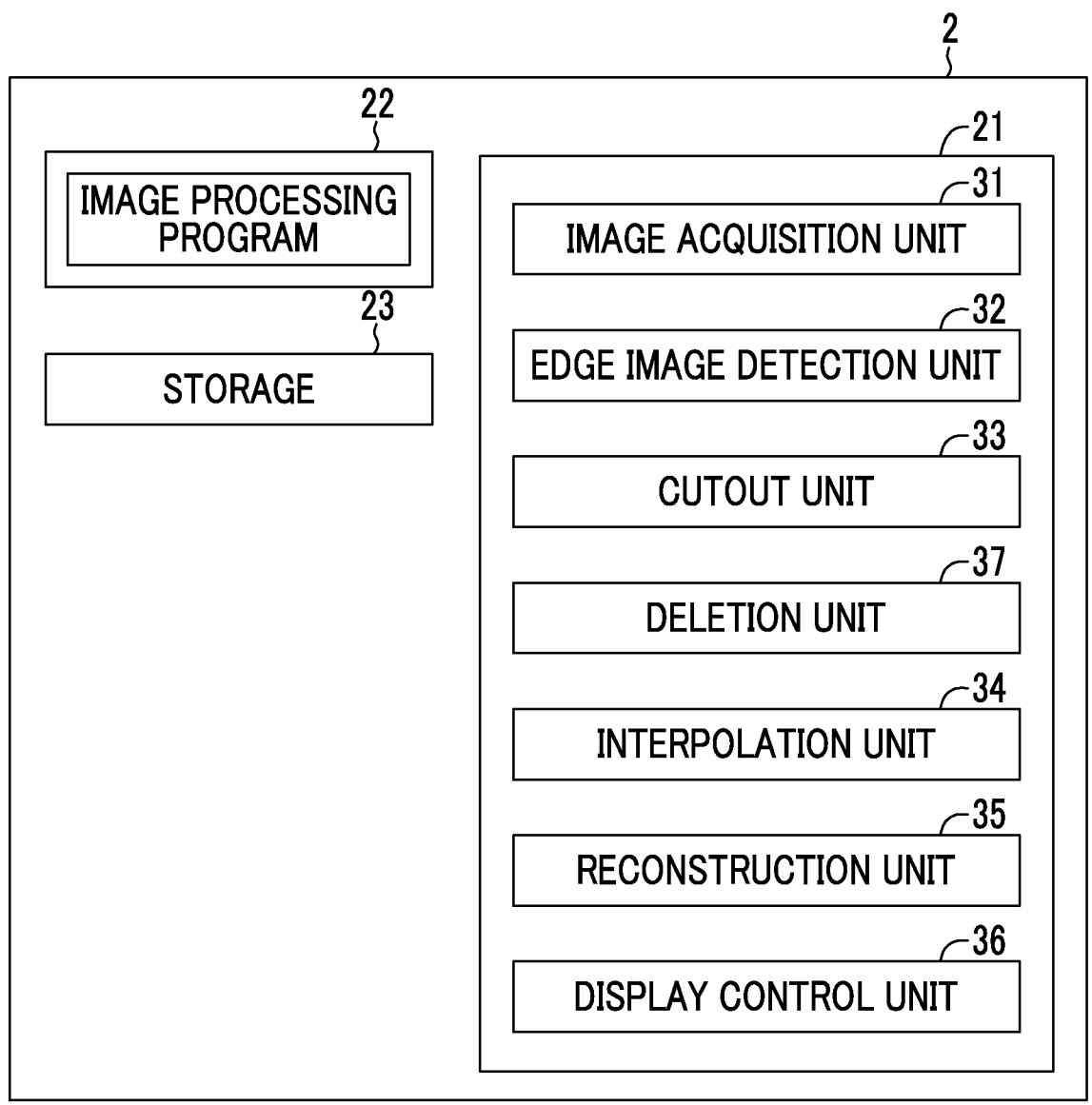
FIG. 18 is a diagram schematically illustrating the configuration of an image processing apparatus implemented by installing an image processing program in a computer configuring a console in a third embodiment.

Next, a third embodiment of the present disclosure will be described. FIG. 18 is a diagram schematically illustrating the configuration of an image processing apparatus implemented by installing an image processing program according to the third embodiment in the computer forming the console 2. In FIG. 18, the same components as those in FIG. 3 are denoted by the same reference numerals and the detailed description thereof will not be repeated. As illustrated in FIG. 18, the image processing apparatus according to the third embodiment is different from that according the first embodiment in that it comprises a deletion unit 37. A process performed by the cutout unit 33 is also different from that in the first embodiment.

Figure 19:
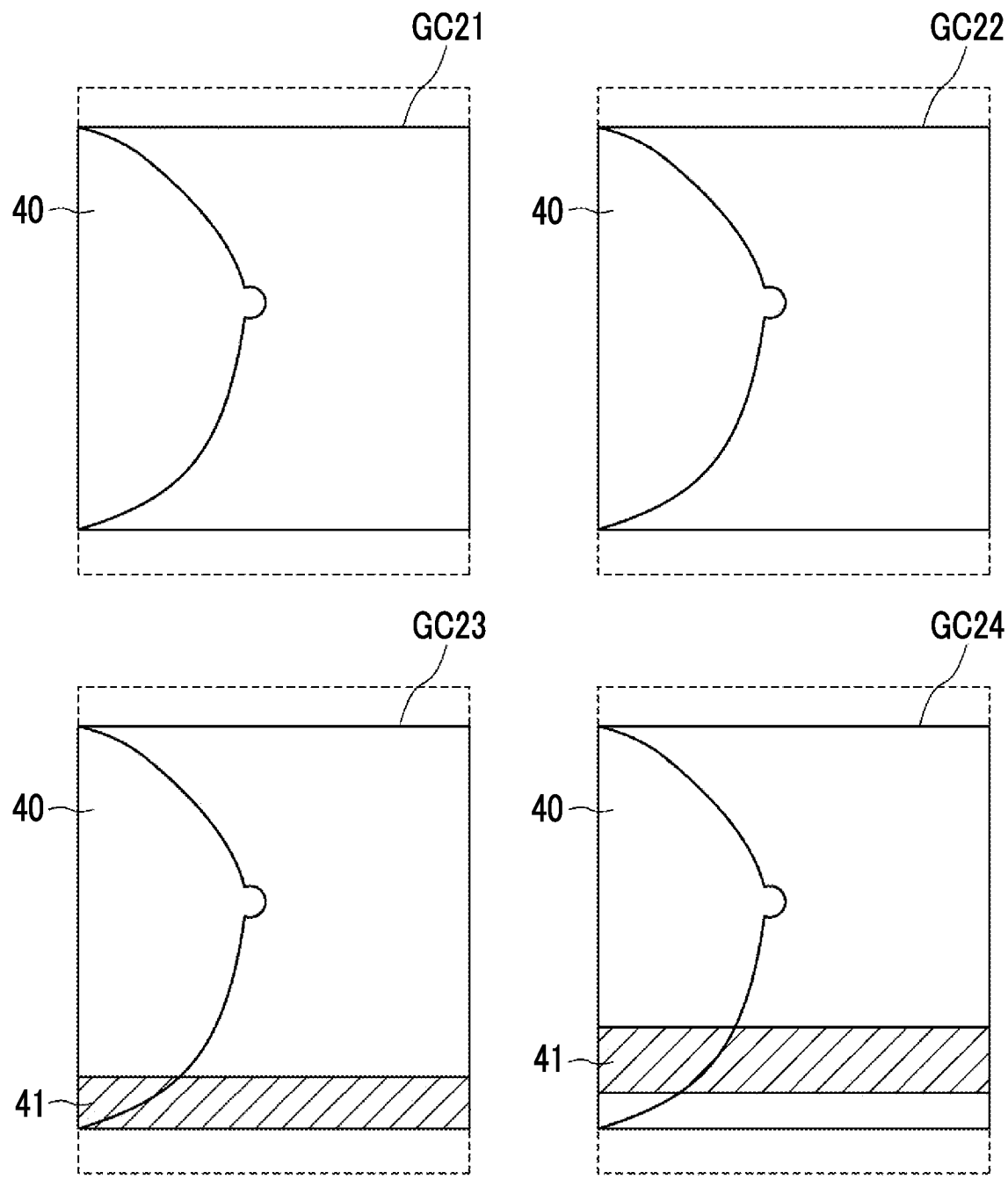
FIG. 19 is a diagram illustrating a cutout process in the third embodiment.

That is, in the third embodiment, the cutout unit 33 generate cut-out projection images GCi by performing the first cutout process of cutting out the projection image Gi on the basis of the contour of the breast image 40 for all the projection images Gi, regardless of whether or not the edge image 41 is included in the projection images Gi. Therefore, cut-out projection images GC21 to GC24 illustrated in FIG. 19 are generated from the projection images GL1 to GL4 illustrated in FIG. 7.

Figure 20:
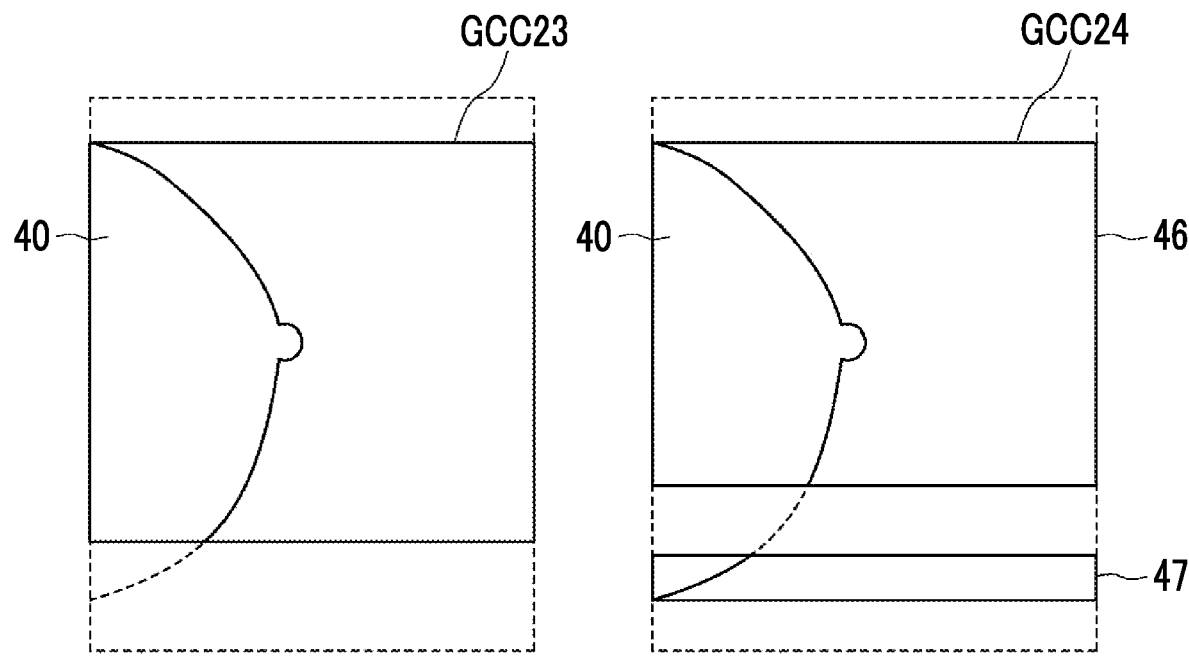
FIG. 20 is a diagram illustrating a deletion process.

In a case in which the edge image 41 is included in the cut-out projection image, the deletion unit 37 deletes the edge image 41 from the cut-out projection image. Here, as illustrated in FIG. 19, the edge images 41 are included in the cut-out projection images GC23 and GC24. Therefore, the deletion unit 37 deletes the edge images 41 from the cut-out projection images GC23 and GC24 to generate deleted cut-out projection images GCC23 and GCC24 as illustrated in FIG. 20. As illustrated in FIG. 20, the deleted cut-out projection image GCC24 is divided into a region 46 and a region 47 which are above and below the edge image 41 in the cut-out projection image GC24, respectively, by the deletion of the edge image 41.

Figure 21:
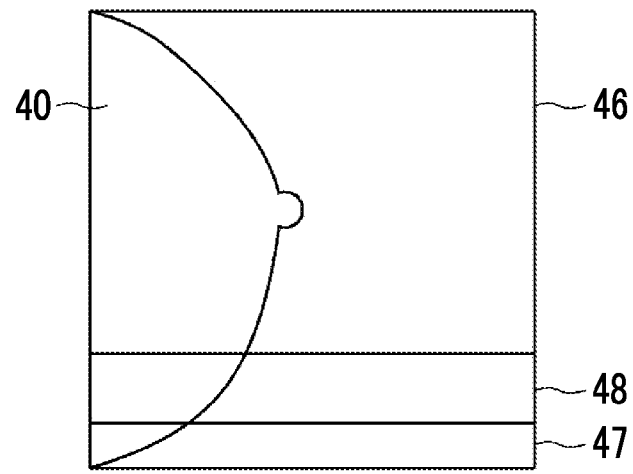
FIG. 21 is a diagram illustrating an interpolation process in the third embodiment.

Here, in the third embodiment, the interpolation unit 34 interpolates the breast image 40 lost by the deletion of the edge image 41 in the deleted cut-out projection images GCC23 and GCC24. In this case, as illustrated in FIG. 21, the interpolation unit 34 interpolates, for example, a partial image 48 cut out from the projection image GL into a region corresponding to the edge image 41 between the upper region 46 and the lower region 47 in the deleted cut-out projection image GCC24. Instead of the interpolation of the partial image 48, the region between the upper region 46 and the lower region 47 may be painted black. Further, the interpolation process may not be performed and the deleted cut-out projection images GCC23 and GCC24 may be stored without any change.

Figure 22:
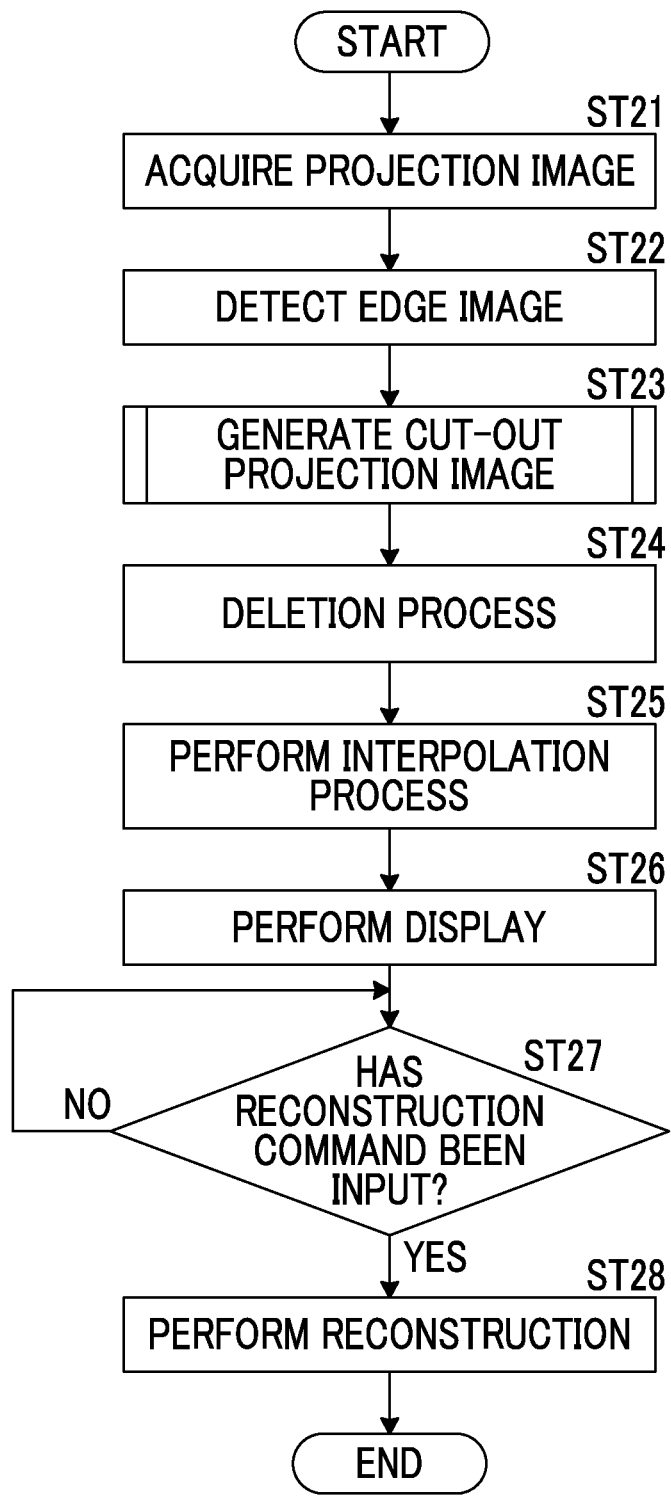
FIG. 22 is a flowchart illustrating a process performed in the third embodiment.

Next, a process performed in the third embodiment will be described. FIG. 22 is a flowchart illustrating the process performed in the third embodiment. It is assumed that the positioning of the breast M on the imaging table 13 has been completed. The process is started by the input of a tomosynthesis imaging command by the operator through the input unit 4 and the image acquisition unit 31 directs the mammography apparatus 10 to perform tomosynthesis imaging to acquire the projection images Gi (Step ST21). Then, the edge image detection unit 32 detects the edge image 41 caused by the compression plate 17 in the plurality of projection images Gi (Step ST22). Then, the cutout unit 33 cuts out the projection image Gi on the basis of the contour of the breast image 40 to generate the cut-out projection image GCi (Step ST23).

Then, in a case in which the edge image 41 is included in the cut-out projection image GCi, the deletion unit 37 deletes the edge image 41 (a deletion process; Step ST24). Then, the interpolation unit 34 interpolates the region of the breast image 40 lost by the deletion process on the basis of at least one of the plurality of projection images Gi (an interpolation process, Step ST25).

Then, the display control unit 36 displays the cut-out projection images GCi while registering the cut-out projection images GCi (Step ST26). Further, monitoring whether or not a reconstruction command has been input by the operator through the input unit 4 is started (Step ST27). In a case in which the monitoring result in Step ST27 is "Yes", the reconstruction unit 35 reconstructs the cut-out projection images GCi to generate a plurality of tomographic images (Step ST28). Then, the process ends. The tomographic images generated by the reconstruction are transmitted to the image server (not illustrated) and then stored therein. Alternatively, the tomographic images are displayed on the display unit 3 by the display control unit 36.

Figure 23:
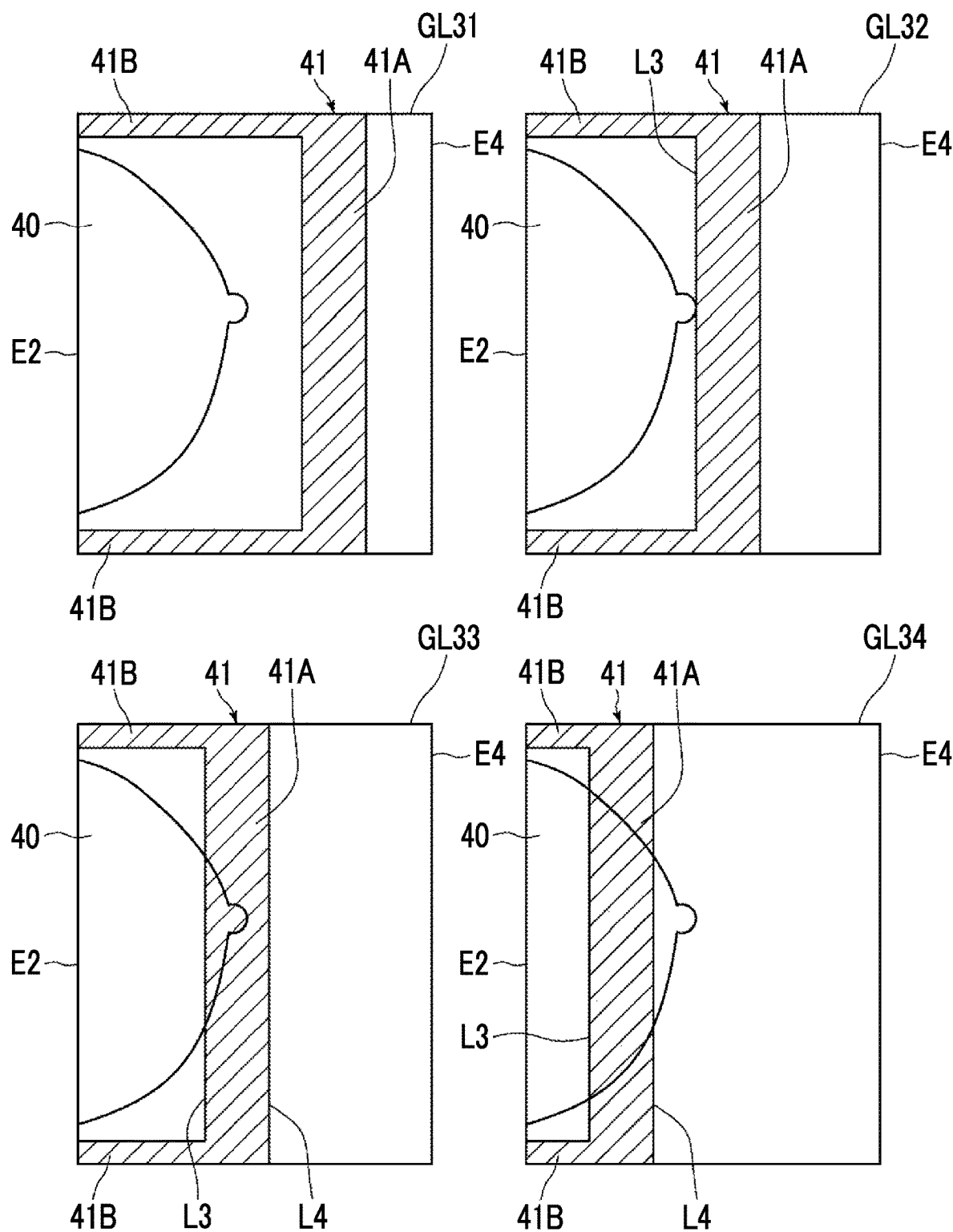
FIG. 23 is a diagram illustrating a projection image including a strip-shaped edge image that extends in the y direction.

In each of the above-described embodiments, in some cases, the edge images 41 and 51 are included on the nipple side of the breast image 40 in the projection image Gi, depending on the type of compression plate 17 and the positional relationship between the compression plate 17 and the breast M. In the first embodiment, in this case, the breast image 40 and the strip-shaped edge image 41 have the four positional relationships (1) to (4). FIG. 23 is a diagram illustrating a projection image in which a strip-shaped edge image extending in the y direction is included on the nipple side of a breast image. In the case of the positional relationship (1), as illustrated in a projection image GL31 of FIG. 23, the breast image 40 is separated from a region (hereinafter, referred to as a vertically long region 41A) which is vertically long, is included in the edge image 41, and extends in the y direction parallel to the left and right sides E2 and E4 of the projection image GL31. In the projection images GL31 to GL34 illustrated in FIG. 23, all of regions (hereinafter, referred to as horizontally long regions 41B) which are horizontally long, are included in the edge images 41, and extend in the x direction have the positional relationship (1). However, the horizontally long region 41B may have any of the positional relationships (2) to (4).

In the case of the positional relationship (2), as illustrated in the projection image GL32 of FIG. 23, the contour (here, the tip of the nipple) of the breast image 40 at a position closest to the right side E4 of the projection image Gi comes into contact with a straight line L3 at a position close to the breast image 40 in the vertically long region 41A included in the edge image 41.

In the case of the positional relationship (3), as illustrated in the projection image GL33 of FIG. 23, the contour of the breast image 40 at the position closest to the right side E4 of the projection image GL33 is superimposed on the vertically long region 41A of the edge image 41.

In the case of the positional relationship (4), as illustrated in the projection image GL34 of FIG. 23, the contour of the breast image 40 at the position closest to the right side E4 of the projection image GL34 is closer to the right side E4 of the projection image GL34 than a straight line L4 at a position closest to the right side E4 of the projection image GL34 in the vertically long region 41A included in the edge image 41.

Even in a case in which the edge image 41 is included on the nipple side of the breast image 40 in the projection image Gi, the cutout unit 33 may perform the cutout process according to the positional relationship between the breast image 40 and the vertically long region 41A of the edge image 41 which extends in the y direction of the projection image Gi on the nipple side of the projection image Gi.

Figure 24:
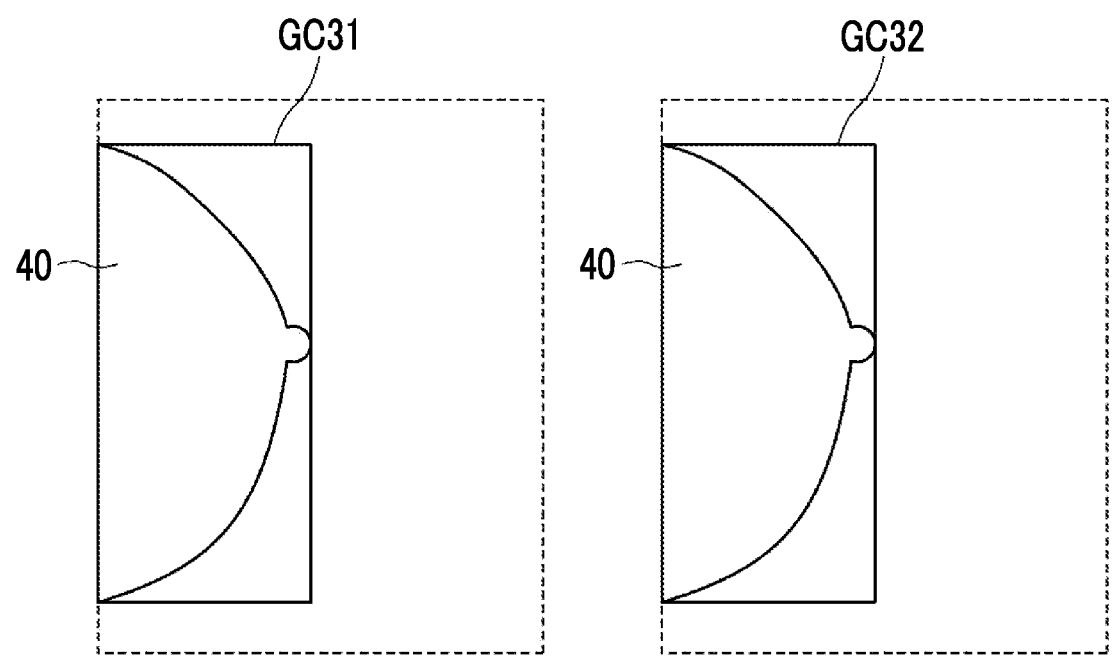
FIG. 24 is a diagram illustrating a cut-out projection image generated from a projection image including a strip-shaped edge image that extends in the y direction.
Figure 24:
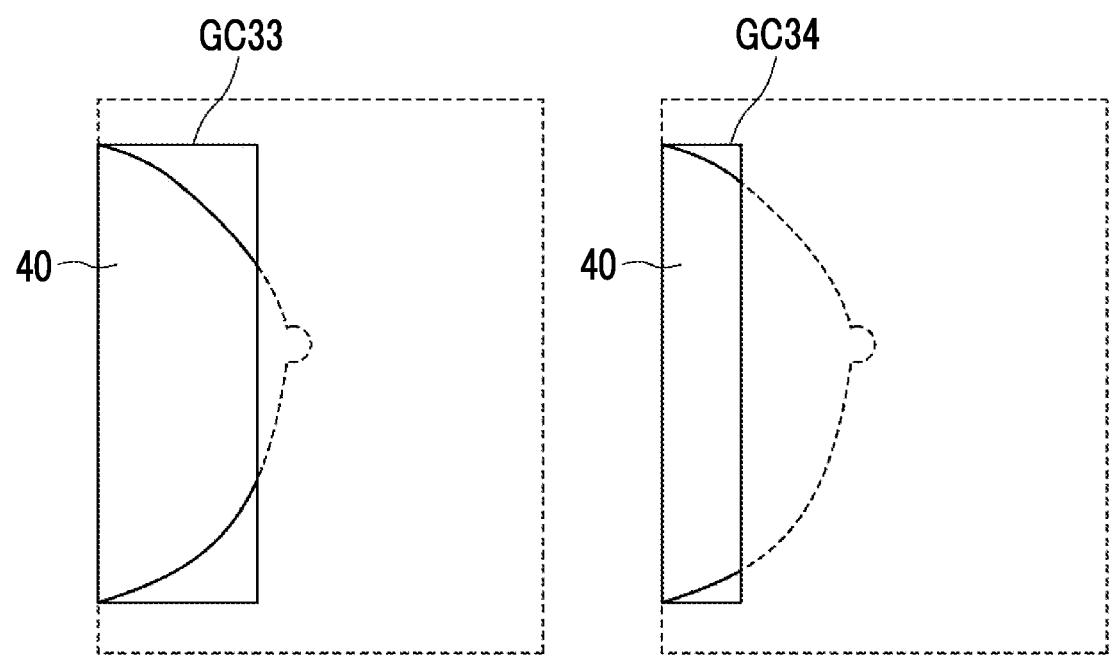

That is, in the case of the positional relationship (1), the cutout unit 33 performs a first cutout process of cutting out the projection image GL31 on the basis of the contour of the breast image 40 to generate a cut-out projection image GC31 illustrated in FIG. 24. That is, the cutout unit 33 cuts out the projection image GL31 along a line that extends in the y direction through the contour of the breast image 40 which is closest to the right side E4 of the projection image GL31 to generate the cut-out projection image GC31. In FIG. 24, the first cutout process is performed in the x direction of the projection image GL31.

In the case of the positional relationship (2), similarly to the case of the positional relationship (1), the cutout unit 33 performs a second cutout process of cutting out the projection image GL32 on the basis of the contour of the breast image 40 to generate a cut-out projection image GC32 illustrated in FIG. 24.

In the case of the positional relationship (3), the cutout unit 33 performs a third cutout process of cutting out the projection image GL33 on the basis of a straight line L3 which is superimposed on the breast image 40 in the vertically long region 41A of the edge image 41 to generates a cut-out projection image GC33 illustrated in FIG. 24.

In the case of the positional relationship (4), the cutout unit 33 performs a fourth cutout process of cutout the projection image GL4 on the basis of a straight line L3, which is the contour of the edge image 41 farther from the contour of the breast image 40 at the position closest to the right side E4 of the projection image GL34, to generate a cut-out projection image GC34 illustrated in FIG. 24.

Figure 25:
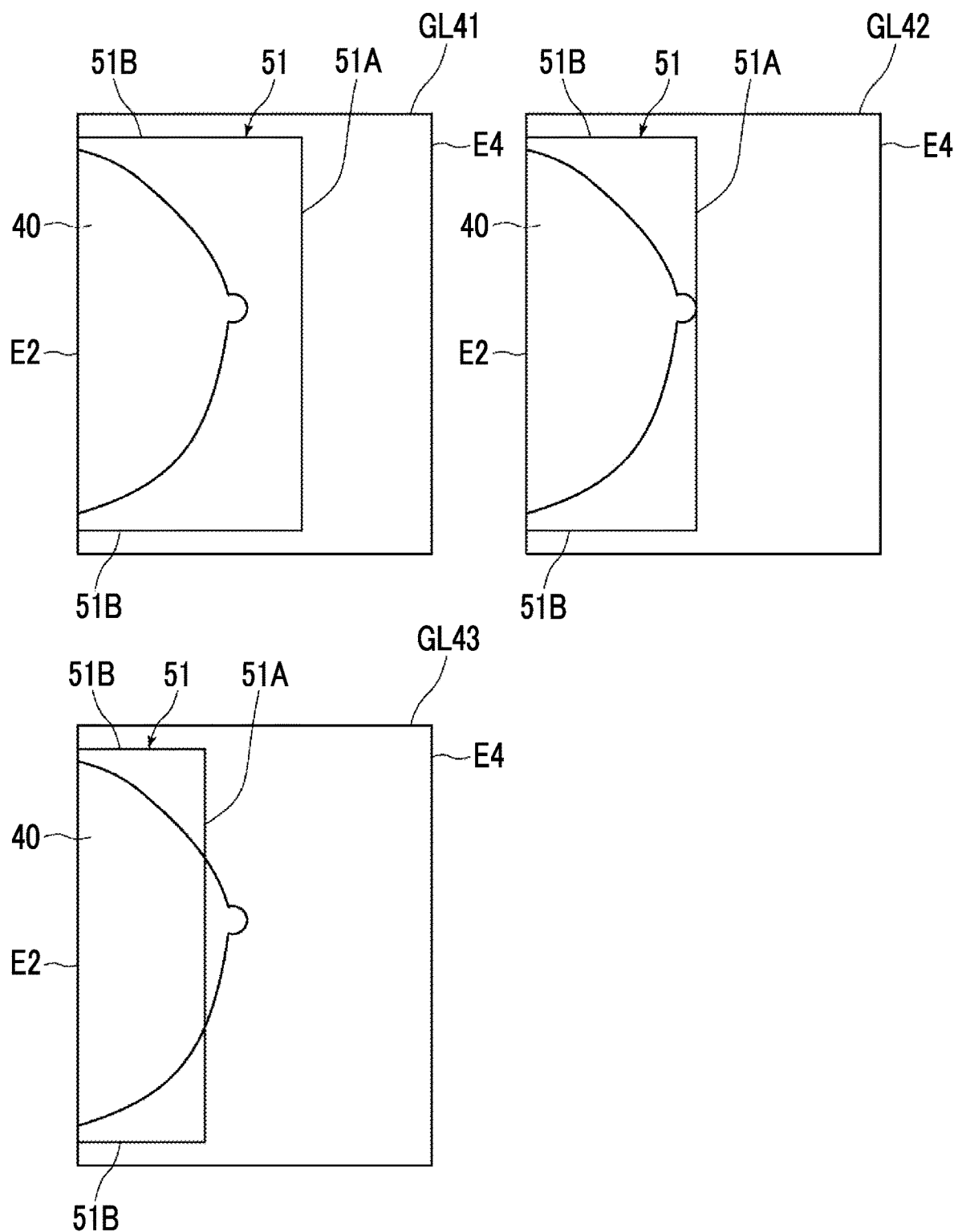
FIG. 25 is a diagram illustrating a projection image including a linear-shaped edge image that extends in the y direction.

In the third embodiment, in some cases, a linear-shaped edge image 51 is also included on the nipple side of the breast image 40. In this case, as in the second embodiment, the breast image 40 and the edge image 41 have three positional relationships (5) to (7). FIG. 25 is a diagram illustrating a projection image in which a linear-shaped edge image extending in the y direction is included on the nipple side of the breast image. In the case of the positional relationship (5), as illustrated in a projection image GL41 of FIG. 25, the breast image 40 is separated from a line (hereinafter, referred to as a vertically long line 51A) which is vertically long and extends in the y direction of the projection image GL41 in an edge image 51. In three projection images GL41 to GL43 illustrated in FIG. 25, all of lines (hereinafter, referred to as horizontally long lines 51B) of the edge image 51 which are horizontally long and extend in the x direction have the positional relationship (5). However, the horizontally long lines 51B may have any of the positional relationships (6) and (7).

In the case of the positional relationship (6), as illustrated in the projection image GL42 of FIG. 25, the contour (here, the tip of the nipple) of the breast image 40 at the position closest to the right side E4 of the projection image GL42 comes into contact with the vertically long line 51A of the edge image 51.

In the case of the positional relationship (7), as illustrated in the projection image GL43 of FIG. 25, the vertically long line 51A of the edge image 51 is superimposed on the breast image 40.

Even in a case in which the linear-shaped edge image 51 is included on the nipple side of the breast image 40 in the projection image Gi, the cutout unit 33 may perform the cutout process according to the positional relationship between the breast image 40 and the vertically long line 51A of the edge image 51 which extends in the y direction of the projection image Gi on the nipple side of the projection image Gi.

Figure 26:
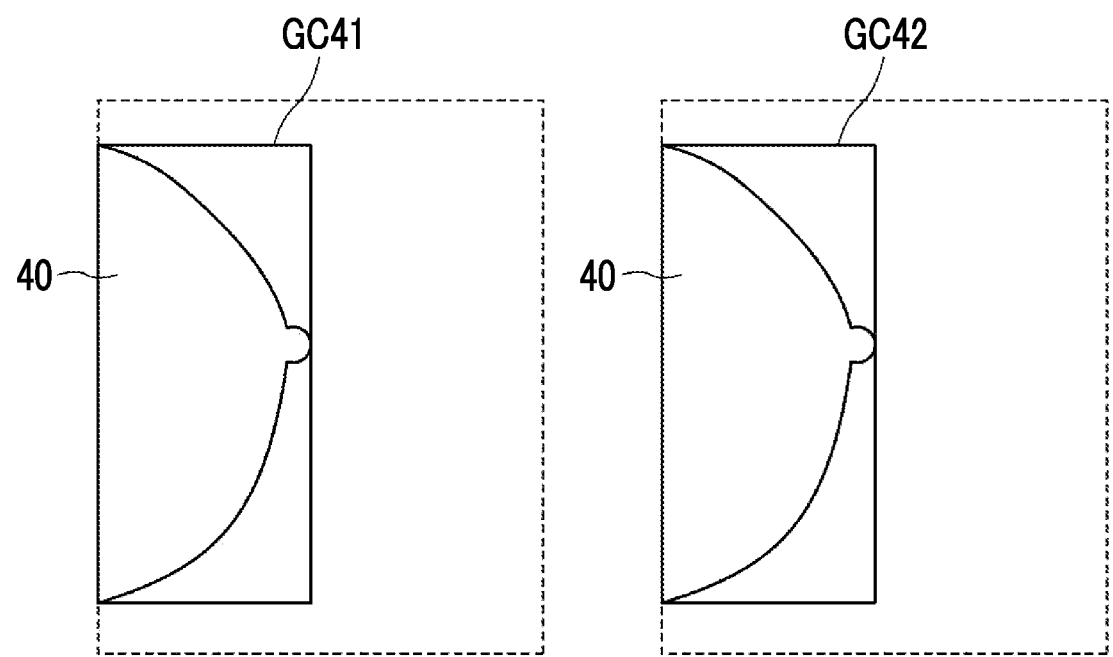
FIG. 26 is a diagram illustrating a cut-out projection image generated from a projection image including a linear-shaped edge image that extends in the y direction.
Figure 26:
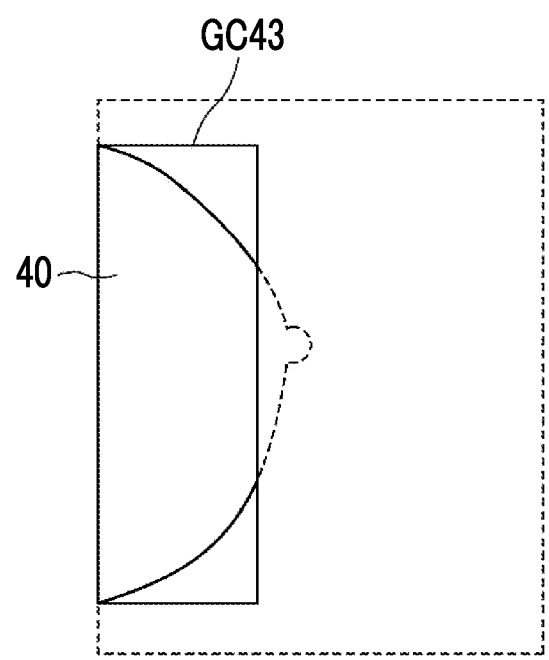

That is, in the case of the positional relationship (5), the cutout unit 33 performs a fifth cutout process of cutting out the projection image GL41 on the basis of the contour of the breast image 40 to generate a cut-out projection image GC41 illustrated in FIG. 26. That is, the cutout unit 33 cuts out the projection image GL41 along a line that extends in the y direction through the contour of the breast image 40 which is closest to the right side E4 of the projection image GL41 to generate the cut-out projection image GC41. In FIG. 26, the fifth cutout process is performed in the x direction of the projection image GL41.

In the case of the positional relationship (6), similarly to the case of the positional relationship (5), the cutout unit 33 performs a sixth cutout process of cutting out the projection image GL42 on the basis of the contour of the breast image 40 to generate a cut-out projection image GC42 illustrated in FIG. 26.

In the case of the positional relationship (7), the cutout unit 33 performs a seventh cutout process of cutting out the projection image GL43 on the basis of the vertically long line 51A of the edge image 51 to generate a cut-out projection image GC43 illustrated in FIG. 26.

The interpolation unit 34 may perform the interpolation process for the cut-out projection image GC33 illustrated in FIG. 24 and the cut-out projection image GC43 illustrated in FIG. 26, as in the first and third embodiments.

Further, in each of the above-described embodiments, the interpolation unit 34 interpolates the region of the breast image 40 lost due to the cutout process or the deletion process. However, the interpolation process of the interpolation unit 34 may not be performed and, for example, a process of displaying and reconstructing the cut-out projection images GCi may be performed.

In each of the above-described embodiments, the trajectory of the radiation source 16 is an arc. However, the trajectory of the radiation source 16 may be a straight line. In addition, the present disclosure can be applied to a case in which tomosynthesis imaging that moves both the radiation source 16 and the radiation detector 15 is performed as described, for example, in U.S. Pat. No. 7,123,684B and "Digital Tomosynthesis in Breast Imaging, Niklason et al., Breast Imaging, Radiography 1997".

In each of the above-described embodiments, the radiation is not particularly limited and, for example, α-rays or γ-rays can be applied in addition to X-rays.

Further, in each of the above-described embodiments, for example, the following various processors can be used as the hardware structure of processing units performing various processes, such as the image acquisition unit 31, the edge image detection unit 32, the cutout unit 33, the interpolation unit 34, the reconstruction unit 35, the display control unit 36, and the deletion unit 37. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. An image processing apparatus comprising at least one processor, wherein the processor is configured to:
  acquire a plurality of projection images corresponding to
    each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;

detect an edge image caused by an edge of the compression plate in the plurality of projection images; and cut out the projection image according to a positional relationship between the edge image and an image of the object to generate a cut-out projection image.

2. The image processing apparatus according to claim 1, wherein the processor is configured to cut out the projection image on the basis of a contour of the object or a contour of the edge image according to the positional relationship between the edge image and the image of the object.

3. The image processing apparatus according to claim 1, wherein, in a case in which the edge image has a strip shape and the image of the object and the edge image are separated from each other in each of the projection images, the processor is configured to perform a first cutout process of cutting out the projection image on the basis of the contour of the object, in a case in which the image of the object and the edge image come into contact with each other without being superimposed, the processor is configured to perform a second cutout process of cutting out the projection image on the basis of the contour of the object, in a case in which a contour of the image of the object at a position closest to a side edge of the projection image is superimposed on the edge image, the processor is configured to perform a third cutout process of cutting out the projection image on the basis of a contour of the edge image which is superimposed on the image of the object, and in a case in which the image of the object and the edge image are superimposed on each other and the image of the object is present on both sides of the edge image, the processor is configured to perform a fourth cutout process of cutting out the projection image on the basis of a contour of the edge image which is far from the contour of the image of the object at the position closest to the side edge of the projection image.

4. The image processing apparatus according to claim 3, wherein the processor is configured to interpolate a region of the image of the object which has been lost by the third cutout process or the fourth cutout process in the cut-out projection image generated by the third cutout process or the fourth cutout process on the basis of at least one of the plurality of projection images.

5. The image processing apparatus according to claim 1, wherein, in a case in which the edge image has a linear shape and the image of the object and the edge image are separated from each other in each of the projection images, the processor is configured to perform a fifth cutout process of cutting out the projection image on the basis of the contour of the object, in a case in which the image of the object and the edge image come into contact with each other, the processor is configured to perform a sixth cutout process of cutting out the projection image on the basis of the contour of the object, and in a case in which the image of the object and the edge image are superimposed on each other, the processor is configured to perform a seventh cutout process of cutting out the projection image on the basis of the edge image.

6. The image processing apparatus according to claim 1, wherein, in a case in which the compression plate has a rectangular shape and the radiation source is relatively moved in a direction intersecting a set of opposite edges of the compression plate, the processor is configured to detect at least the edge image caused by the set of edges of the compression plate.

7. The image processing apparatus according to claim 1, wherein the processor is configured to register the plurality of cut-out projection images on the basis of a common reference position in the plurality of projection images and displays the plurality of cut-out projection images on a display unit.

8. The image processing apparatus according to claim 1, wherein the processor is configured to reconstruct the cut-out projection images to generate tomographic images in each of a plurality of tomographic planes of the object.

9. The image processing apparatus according to claim 1, wherein the object is a breast.

10. An image processing apparatus comprising at least one processor, wherein the processor is configured to:

acquire a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;

detect an edge image caused by an edge of the compression plate in the plurality of projection images;

cut out the projection image on the basis of a contour of the object in each of the projection images to generate a cut-out projection image; and delete the edge image in a case in which the edge image is included in the cut-out projection image.

11. The image processing apparatus according to claim 10, wherein the processor is configured to interpolate a region of an image of the object which has been lost by the deletion of the edge image in the cut-out projection image obtained by deleting the edge image, on the basis of at least one of the plurality of projection images.

12. The image processing apparatus according to claim 10, wherein, in a case in which the compression plate has a rectangular shape and the radiation source is relatively moved in a direction intersecting a set of opposite edges of the compression plate, the processor is configured to detect at least the edge image caused by the set of edges of the compression plate.

13. The image processing apparatus according to claim 10, wherein the processor is configured to register the plurality of cut-out projection images on the basis of a common reference position in the plurality of projection images and displays the plurality of cut-out projection images on a display unit.

14. The image processing apparatus according to claim 10, wherein the processor is configured to reconstruct the cut-out projection images to generate tomographic images in each of a plurality of tomographic planes of the object.

15. The image processing apparatus according to claim 10,
wherein the object is a breast.

16. An image processing method comprising:
acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;
detecting an edge image caused by an edge of the compression plate in the plurality of projection images; and
cutting out the projection image according to a positional relationship between the edge image and an image of the object to generate a cut-out projection image.

17. An image processing method comprising:
acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;
detecting an edge image caused by an edge of the compression plate in the plurality of projection images;
cutting out the projection image on the basis of a contour of the object in each of the projection images to generate a cut-out projection image; and
deleting the edge image in a case in which the edge image is included in the cut-out projection image.

18. A non-transitory computer-readable recording medium having stored therein an image processing program that causes a computer to perform:
a step of acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;
a step of detecting an edge image caused by an edge of the compression plate in the plurality of projection images; and
a step of cutting out the projection image according to a positional relationship between the edge image and an image of the object to generate a cut-out projection image.

19. A non-transitory computer-readable recording medium having stored therein an image processing program that causes a computer to perform:
a step of acquiring a plurality of projection images corresponding to each of a plurality of radiation source positions which have been generated by directing an imaging apparatus to perform tomosynthesis imaging that relatively moves a radiation source with respect to a detection unit and irradiates an object compressed by a compression plate with radiation at the plurality of radiation source positions caused by the movement of the radiation source;
a step of detecting an edge image caused by an edge of the compression plate in the plurality of projection images;
a step of cutting out the projection image on the basis of an edge of the object in each of the projection images to generate a cut-out projection image; and
a step of deleting the edge image in a case in which the edge image is included in the cut-out projection image.

* * * * *